US008529563B2

(12) United States Patent
Long et al.

(10) Patent No.: US 8,529,563 B2
(45) Date of Patent: Sep. 10, 2013

(54) ELECTRICAL ABLATION DEVICES

(75) Inventors: Gary L. Long, Cincinnati, OH (US);
David N. Plescia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1168 days.

(21) Appl. No.: 12/197,749

(22) Filed: Aug. 25, 2008

(65) Prior Publication Data
US 2010/0049190 A1 Feb. 25, 2010

(51) Int. Cl.
*A61B 18/18* (2006.01)

(52) U.S. Cl.
USPC .......................................... 606/41

(58) Field of Classification Search
USPC ................ 606/32–34, 108, 41; 604/174, 175
See application file for complete search history.

(56) References Cited

U.S. PATENT DOCUMENTS

| 645,576 A | 3/1900 | Tesla |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |

(Continued)

FOREIGN PATENT DOCUMENTS

| AU | 666310 B2 | 2/1996 |
| DE | 3008120 A1 | 9/1980 |

(Continued)

OTHER PUBLICATIONS

Written Opinion for PCT/US2009/054453, Mar. 23, 2010 (9 pages).

(Continued)

*Primary Examiner* — Theodore Stigell

(57) ABSTRACT

A connector configured to receive electrical energy from an energy source. A fastener is coupled to the connector. The fastener is configured for attachment through a tissue wall. A first electrode includes at least one electrically conductive portion and is coupled to the connector by a first electrically conductive wire.

6 Claims, 21 Drawing Sheets

(56) References Cited

U.S. PATENT DOCUMENTS

| | | | |
|---|---|---|---|
| 4,085,743 A | 4/1978 | Yoon | |
| 4,164,225 A | 8/1979 | Johnson et al. | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,269,174 A | 5/1981 | Adair | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,406,656 A | 9/1983 | Hattler et al. | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,655,219 A | 4/1987 | Petruzzi | |
| 4,669,470 A | 6/1987 | Brandfield | |
| 4,671,477 A | 6/1987 | Cullen | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,733,662 A | 3/1988 | DeSatnick et al. | |
| D295,894 S | 5/1988 | Sharkany et al. | |
| 4,763,669 A | 8/1988 | Jaeger | |
| 4,770,188 A | 9/1988 | Chikama | |
| 4,815,450 A | 3/1989 | Patel | |
| 4,823,794 A | 4/1989 | Pierce | |
| 4,829,999 A | 5/1989 | Auth | |
| 4,867,140 A | 9/1989 | Hovis et al. | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,960,133 A | 10/1990 | Hewson | |
| 4,977,887 A | 12/1990 | Gouda | |
| 4,979,950 A | 12/1990 | Transue et al. | |
| 4,984,581 A | 1/1991 | Stice | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,201,752 A | 4/1993 | Brown et al. | |
| 5,201,908 A | 4/1993 | Jones | |
| 5,203,785 A | 4/1993 | Slater | |
| 5,203,787 A | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A | 6/1993 | Bendel et al. | |
| 5,222,362 A | 6/1993 | Maus et al. | |
| 5,222,965 A | 6/1993 | Haughton | |
| 5,234,437 A | 8/1993 | Sepetka | |
| 5,234,453 A | 8/1993 | Smith et al. | |
| 5,235,964 A | 8/1993 | Abenaim | |
| 5,242,456 A | 9/1993 | Nash et al. | |
| 5,246,424 A | 9/1993 | Wilk | |
| 5,259,366 A | 11/1993 | Reydel et al. | |
| 5,263,958 A | 11/1993 | deGuillebon et al. | |
| 5,273,524 A | 12/1993 | Fox et al. | |
| 5,275,607 A | 1/1994 | Lo et al. | |
| 5,284,128 A | 2/1994 | Hart | |
| 5,284,162 A | 2/1994 | Wilk | |
| 5,287,845 A | 2/1994 | Faul et al. | |
| 5,290,299 A | 3/1994 | Fain et al. | |
| 5,290,302 A | 3/1994 | Pericic | |
| 5,295,977 A | 3/1994 | Cohen et al. | |
| 5,297,536 A | 3/1994 | Wilk | |
| 5,301,061 A | 4/1994 | Nakada et al. | |
| 5,312,333 A | 5/1994 | Churinetz et al. | |
| 5,312,351 A | 5/1994 | Gerrone | |
| 5,312,416 A | 5/1994 | Spaeth et al. | |
| 5,312,423 A | 5/1994 | Rosenbluth et al. | |
| 5,320,636 A | 6/1994 | Slater | |
| 5,325,845 A | 7/1994 | Adair | |
| 5,330,471 A | 7/1994 | Eggers | |
| 5,330,486 A | 7/1994 | Wilk | |
| 5,330,488 A | 7/1994 | Goldrath | |
| 5,330,496 A | 7/1994 | Alferness | |
| 5,330,502 A | 7/1994 | Hassler et al. | |
| 5,331,971 A | 7/1994 | Bales et al. | |
| 5,334,198 A | 8/1994 | Hart et al. | |
| 5,344,428 A | 9/1994 | Griffiths | |
| 5,350,391 A | 9/1994 | Iacovelli | |
| 5,352,184 A | 10/1994 | Goldberg et al. | |
| 5,352,222 A | 10/1994 | Rydell | |
| 5,354,302 A | 10/1994 | Ko | |
| 5,354,311 A | 10/1994 | Kambin et al. | |
| 5,356,408 A | 10/1994 | Rydell | |
| 5,364,408 A | 11/1994 | Gordon | |
| 5,364,410 A | 11/1994 | Failla et al. | |
| 5,366,466 A | 11/1994 | Christian et al. | |
| 5,366,467 A | 11/1994 | Lynch et al. | |
| 5,368,605 A | 11/1994 | Miller, Jr. | |
| 5,370,647 A | 12/1994 | Graber et al. | |
| 5,370,679 A | 12/1994 | Atlee, III | |
| 5,374,273 A | 12/1994 | Nakao et al. | |
| 5,374,275 A | 12/1994 | Bradley et al. | |
| 5,374,277 A | 12/1994 | Hassler | |
| 5,377,695 A | 1/1995 | An Haack | |
| 5,383,877 A | 1/1995 | Clarke | |
| 5,383,888 A | 1/1995 | Zvenyatsky et al. | |
| 5,386,817 A | 2/1995 | Jones | |
| 5,391,174 A | 2/1995 | Weston | |
| 5,392,789 A | 2/1995 | Slater et al. | |
| 5,395,386 A | 3/1995 | Slater | |
| 5,401,248 A | 3/1995 | Bencini | |
| 5,403,328 A | 4/1995 | Shallman | |
| 5,403,342 A | 4/1995 | Tovey et al. | |
| 5,403,348 A | 4/1995 | Bonutti | |
| 5,405,073 A | 4/1995 | Porter | |
| 5,405,359 A | 4/1995 | Pierce | |
| 5,409,478 A | 4/1995 | Gerry et al. | |
| 5,417,699 A | 5/1995 | Klein et al. | |
| 5,423,821 A | 6/1995 | Pasque | |
| 5,433,721 A | 7/1995 | Hooven et al. | |
| 5,439,471 A | 8/1995 | Kerr | |
| 5,439,478 A | 8/1995 | Palmer | |
| 5,441,059 A | 8/1995 | Dannan | |
| 5,441,499 A | 8/1995 | Fritzsch | |
| 5,443,463 A | 8/1995 | Stern et al. | |
| 5,445,638 A | 8/1995 | Rydell et al. | |
| 5,449,021 A | 9/1995 | Chikama | |

| | | | | | | |
|---|---|---|---|---|---|---|
| 5,456,667 A | 10/1995 | Ham et al. | | 5,700,275 A | 12/1997 | Bell et al. |
| 5,456,684 A | 10/1995 | Schmidt et al. | | 5,702,438 A | 12/1997 | Avitall |
| 5,458,131 A | 10/1995 | Wilk | | 5,704,892 A | 1/1998 | Adair |
| 5,458,583 A | 10/1995 | McNeely et al. | | 5,709,708 A | 1/1998 | Thal |
| 5,460,168 A | 10/1995 | Masubuchi et al. | | 5,716,326 A | 2/1998 | Dannan |
| 5,460,629 A | 10/1995 | Shlain et al. | | 5,730,740 A | 3/1998 | Wales et al. |
| 5,462,561 A | 10/1995 | Voda | | 5,735,849 A | 4/1998 | Baden et al. |
| 5,465,731 A | 11/1995 | Bell et al. | | 5,741,234 A * | 4/1998 | Aboul-Hosn ................. 604/174 |
| 5,467,763 A | 11/1995 | McMahon et al. | | 5,741,278 A | 4/1998 | Stevens |
| 5,468,250 A | 11/1995 | Paraschac et al. | | 5,741,285 A | 4/1998 | McBrayer et al. |
| 5,470,308 A | 11/1995 | Edwards et al. | | 5,746,759 A | 5/1998 | Meade et al. |
| 5,470,320 A | 11/1995 | Tiefenbrun et al. | | 5,749,881 A | 5/1998 | Sackier et al. |
| 5,478,347 A | 12/1995 | Aranyi | | 5,749,889 A | 5/1998 | Bacich et al. |
| 5,480,404 A | 1/1996 | Kammerer et al. | | 5,752,951 A | 5/1998 | Yanik |
| 5,482,054 A | 1/1996 | Slater et al. | | 5,755,731 A | 5/1998 | Grinberg |
| 5,484,451 A | 1/1996 | Akopov et al. | | 5,766,167 A | 6/1998 | Eggers et al. |
| 5,489,256 A | 2/1996 | Adair | | 5,766,170 A | 6/1998 | Eggers |
| 5,496,347 A | 3/1996 | Hashiguchi et al. | | 5,766,205 A | 6/1998 | Zvenyatsky et al. |
| 5,499,990 A | 3/1996 | Schülken et al. | | 5,769,849 A | 6/1998 | Eggers |
| 5,499,992 A | 3/1996 | Meade et al. | | 5,779,701 A | 7/1998 | McBrayer et al. |
| 5,501,692 A | 3/1996 | Riza | | 5,779,716 A | 7/1998 | Cano et al. |
| 5,503,616 A | 4/1996 | Jones | | 5,779,727 A | 7/1998 | Orejola |
| 5,505,686 A | 4/1996 | Willis et al. | | 5,782,859 A | 7/1998 | Nicholas et al. |
| 5,507,755 A | 4/1996 | Gresl et al. | | 5,782,866 A | 7/1998 | Wenstrom, Jr. |
| 5,511,564 A | 4/1996 | Wilk | | 5,791,022 A | 8/1998 | Bohman |
| 5,514,157 A | 5/1996 | Nicholas et al. | | 5,792,113 A | 8/1998 | Kramer et al. |
| 5,522,829 A | 6/1996 | Michalos | | 5,792,153 A | 8/1998 | Swain et al. |
| 5,522,830 A | 6/1996 | Aranyi | | 5,792,165 A | 8/1998 | Klieman et al. |
| 5,527,321 A | 6/1996 | Hinchliffe | | 5,797,835 A | 8/1998 | Green |
| 5,536,248 A | 7/1996 | Weaver et al. | | 5,797,928 A | 8/1998 | Kogasaka |
| 5,540,648 A | 7/1996 | Yoon | | 5,797,939 A | 8/1998 | Yoon |
| 5,554,151 A | 9/1996 | Hinchliffe | | 5,797,941 A | 8/1998 | Schulze et al. |
| 5,555,883 A | 9/1996 | Avitall | | 5,803,903 A | 9/1998 | Athas et al. |
| 5,558,133 A | 9/1996 | Bortoli et al. | | 5,808,665 A | 9/1998 | Green |
| 5,562,693 A | 10/1996 | Devlin et al. | | 5,810,806 A | 9/1998 | Ritchart et al. |
| 5,569,243 A | 10/1996 | Kortenbach et al. | | 5,810,849 A | 9/1998 | Kontos |
| 5,569,298 A | 10/1996 | Schnell | | 5,810,865 A | 9/1998 | Koscher et al. |
| 5,573,540 A | 11/1996 | Yoon | | 5,810,876 A | 9/1998 | Kelleher |
| 5,578,030 A | 11/1996 | Levin | | 5,810,877 A | 9/1998 | Roth et al. |
| 5,582,611 A | 12/1996 | Tsuruta et al. | | 5,813,976 A | 9/1998 | Filipi et al. |
| 5,582,617 A | 12/1996 | Klieman et al. | | 5,814,058 A | 9/1998 | Carlson et al. |
| 5,584,845 A | 12/1996 | Hart | | 5,817,061 A | 10/1998 | Goodwin et al. |
| 5,591,179 A | 1/1997 | Edelstein | | 5,817,107 A | 10/1998 | Schaller |
| 5,593,420 A | 1/1997 | Eubanks, Jr et al. | | 5,817,119 A | 10/1998 | Klieman et al. |
| 5,595,562 A | 1/1997 | Grier | | 5,819,736 A | 10/1998 | Avny et al. |
| 5,597,378 A | 1/1997 | Jervis | | 5,824,071 A | 10/1998 | Nelson et al. |
| 5,601,573 A | 2/1997 | Fogelberg et al. | | 5,827,281 A | 10/1998 | Levin |
| 5,601,588 A | 2/1997 | Tonomura et al. | | 5,827,299 A | 10/1998 | Thomason et al. |
| 5,604,531 A | 2/1997 | Iddan et al. | | 5,830,231 A | 11/1998 | Geiges, Jr. |
| 5,607,389 A | 3/1997 | Edwards et al. | | 5,833,700 A | 11/1998 | Fogelberg et al. |
| 5,607,450 A | 3/1997 | Zvenyatsky et al. | | 5,833,703 A | 11/1998 | Manushakian |
| 5,613,975 A | 3/1997 | Christy | | 5,843,017 A | 12/1998 | Yoon |
| 5,618,303 A | 4/1997 | Marlow et al. | | 5,843,121 A | 12/1998 | Yoon |
| 5,620,415 A | 4/1997 | Lucey et al. | | 5,849,022 A | 12/1998 | Sakashita et al. |
| 5,624,399 A | 4/1997 | Ackerman | | 5,853,374 A | 12/1998 | Hart et al. |
| 5,624,431 A | 4/1997 | Gerry et al. | | 5,855,585 A | 1/1999 | Kontos |
| 5,626,578 A | 5/1997 | Tihon | | 5,860,913 A | 1/1999 | Yamaya et al. |
| 5,628,732 A | 5/1997 | Antoon, Jr. et al. | | 5,860,995 A | 1/1999 | Berkelaar |
| 5,630,782 A | 5/1997 | Adair | | 5,868,762 A | 2/1999 | Cragg et al. |
| 5,643,283 A | 7/1997 | Younker | | 5,876,411 A | 3/1999 | Kontos |
| 5,643,292 A | 7/1997 | Hart | | 5,882,331 A | 3/1999 | Sasaki |
| 5,643,294 A | 7/1997 | Tovey et al. | | 5,882,344 A | 3/1999 | Stouder, Jr. |
| 5,644,798 A | 7/1997 | Shah | | 5,893,846 A | 4/1999 | Bales et al. |
| 5,645,083 A | 7/1997 | Essig et al. | | 5,893,874 A | 4/1999 | Bourque et al. |
| 5,645,565 A | 7/1997 | Rudd et al. | | 5,893,875 A | 4/1999 | O'Connor et al. |
| 5,649,372 A | 7/1997 | Souza | | 5,899,919 A | 5/1999 | Eubanks, Jr. et al. |
| 5,653,677 A | 8/1997 | Okada et al. | | 5,902,254 A | 5/1999 | Magram |
| 5,653,690 A | 8/1997 | Booth et al. | | 5,904,702 A | 5/1999 | Ek et al. |
| 5,653,722 A | 8/1997 | Kieturakis | | 5,908,420 A | 6/1999 | Parins et al. |
| 5,662,663 A | 9/1997 | Shallman | | 5,911,737 A | 6/1999 | Lee et al. |
| 5,669,875 A | 9/1997 | van Eerdenburg | | 5,916,147 A | 6/1999 | Boury |
| 5,681,324 A | 10/1997 | Kammerer et al. | | 5,921,993 A | 7/1999 | Yoon |
| 5,681,330 A | 10/1997 | Hughett et al. | | 5,921,997 A | 7/1999 | Fogelberg et al. |
| 5,685,820 A | 11/1997 | Riek et al. | | 5,922,008 A | 7/1999 | Gimpelson |
| 5,690,656 A | 11/1997 | Cope et al. | | 5,925,052 A | 7/1999 | Simmons |
| 5,690,660 A | 11/1997 | Kauker et al. | | 5,928,255 A | 7/1999 | Meade et al. |
| 5,695,448 A | 12/1997 | Kimura et al. | | 5,928,266 A | 7/1999 | Kontos |
| 5,695,505 A | 12/1997 | Yoon | | 5,936,536 A | 8/1999 | Morris |
| 5,695,511 A | 12/1997 | Cano et al. | | 5,944,718 A | 8/1999 | Austin et al. |

| | | |
|---|---|---|
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,989,182 A | 11/1999 | Hori et al. |
| 5,993,447 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,634 A | 2/2000 | Wu et al. |
| 6,033,399 A | 3/2000 | Gines |
| 6,036,685 A | 3/2000 | Mueller |
| 6,053,927 A | 4/2000 | Hamas |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,108 A | 7/2000 | McBrayer et al. |
| 6,096,046 A | 8/2000 | Weiss |
| 6,102,926 A | 8/2000 | Tartaglia et al. |
| 6,106,473 A | 8/2000 | Violante et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,159,200 A | 12/2000 | Verdura et al. |
| 6,165,184 A | 12/2000 | Verdura et al. |
| 6,168,570 B1 | 1/2001 | Ferrera |
| 6,168,605 B1 | 1/2001 | Measamer et al. |
| 6,170,130 B1 | 1/2001 | Hamilton et al. |
| 6,179,776 B1 | 1/2001 | Adams et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,214,007 B1 | 4/2001 | Anderson |
| 6,228,096 B1 | 5/2001 | Marchand |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,322,578 B1 | 11/2001 | Houle et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,035 B1 | 3/2002 | Manushakian |
| 6,361,534 B1 | 3/2002 | Chen et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,391,029 B1 | 5/2002 | Hooven et al. |
| 6,402,735 B1 | 6/2002 | Langevin |
| 6,406,440 B1 | 6/2002 | Stefanchik |
| 6,409,733 B1 | 6/2002 | Conlon et al. |
| 6,427,089 B1 | 7/2002 | Knowlton |
| 6,431,500 B1 | 8/2002 | Jacobs et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,520,954 B2 | 2/2003 | Ouchi |
| 6,543,456 B1 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,585,642 B2 | 7/2003 | Christopher |
| 6,585,717 B1 | 7/2003 | Wittenberger et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |

| | | |
|---|---|---|
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 * | 9/2004 | Chornenky et al. ............... 607/2 |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 * | 5/2005 | Behl et al. ................. 607/99 |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francere et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |

| | | | | | | |
|---|---|---|---|---|---|---|
| 7,344,536 B1 | 3/2008 | Lunsford et al. | 2002/0022771 A1 | 2/2002 | Diokno et al. | |
| 7,352,387 B2 | 4/2008 | Yamamoto | 2002/0022857 A1 | 2/2002 | Goldsteen et al. | |
| 7,364,582 B2 | 4/2008 | Lee | 2002/0023353 A1 | 2/2002 | Ting-Kung | |
| 7,371,215 B2 | 5/2008 | Colliou et al. | 2002/0029055 A1 | 3/2002 | Bonutti | |
| 7,381,216 B2 | 6/2008 | Buzzard et al. | 2002/0032441 A1* | 3/2002 | Ingle et al. | 606/41 |
| 7,393,322 B2 | 7/2008 | Wenchell | 2002/0042562 A1 | 4/2002 | Meron et al. | |
| 7,402,162 B2 | 7/2008 | Ouchi | 2002/0049439 A1 | 4/2002 | Mulier et al. | |
| 7,404,791 B2 | 7/2008 | Linares et al. | 2002/0068945 A1 | 6/2002 | Sixto, Jr. et al. | |
| 7,413,563 B2 | 8/2008 | Corcoran et al. | 2002/0078967 A1 | 6/2002 | Sixto, Jr. et al. | |
| 7,416,554 B2 | 8/2008 | Lam et al. | 2002/0082516 A1 | 6/2002 | Stefanchik | |
| 7,422,590 B2 | 9/2008 | Kupferschmid et al. | 2002/0091391 A1 | 7/2002 | Cole et al. | |
| 7,435,257 B2 | 10/2008 | Lashinski et al. | 2002/0095164 A1 | 7/2002 | Andreas et al. | |
| 7,452,327 B2 | 11/2008 | Durgin et al. | 2002/0107530 A1 | 8/2002 | Sauer et al. | |
| 7,455,208 B2 | 11/2008 | Wales et al. | 2002/0133115 A1 | 9/2002 | Gordon et al. | |
| 7,468,066 B2 | 12/2008 | Vargas et al. | 2002/0137997 A1* | 9/2002 | Mastrototaro et al. | 600/345 |
| 7,488,295 B2 | 2/2009 | Burbank et al. | 2002/0138086 A1 | 9/2002 | Sixto, Jr. et al. | |
| 7,497,867 B2 | 3/2009 | Lasner et al. | 2002/0147456 A1 | 10/2002 | Diduch et al. | |
| 7,507,200 B2 | 3/2009 | Okada | 2002/0183591 A1 | 12/2002 | Matsuura et al. | |
| 7,524,281 B2 | 4/2009 | Chu et al. | 2003/0023255 A1 | 1/2003 | Miles et al. | |
| 7,524,302 B2 | 4/2009 | Tower | 2003/0036679 A1 | 2/2003 | Kortenbach et al. | |
| 7,534,228 B2 | 5/2009 | Williams | 2003/0069602 A1 | 4/2003 | Jacobs et al. | |
| 7,540,872 B2 | 6/2009 | Schechter et al. | 2003/0083681 A1 | 5/2003 | Moutafis et al. | |
| 7,544,203 B2 | 6/2009 | Chin et al. | 2003/0114732 A1 | 6/2003 | Webler et al. | |
| 7,548,040 B2 | 6/2009 | Lee et al. | 2003/0120257 A1 | 6/2003 | Houston et al. | |
| 7,549,564 B2 | 6/2009 | Boudreaux | 2003/0124009 A1 | 7/2003 | Ravi et al. | |
| 7,553,278 B2 | 6/2009 | Kucklick | 2003/0130564 A1 | 7/2003 | Martone et al. | |
| 7,553,298 B2 | 6/2009 | Hunt et al. | 2003/0130656 A1 | 7/2003 | Levin | |
| 7,559,887 B2 | 7/2009 | Dannan | 2003/0158521 A1 | 8/2003 | Ameri | |
| 7,559,916 B2 | 7/2009 | Smith et al. | 2003/0167062 A1 | 9/2003 | Gambale et al. | |
| 7,560,006 B2 | 7/2009 | Rakos et al. | 2003/0171651 A1 | 9/2003 | Page et al. | |
| 7,561,916 B2 | 7/2009 | Hunt et al. | 2003/0176880 A1 | 9/2003 | Long et al. | |
| 7,566,334 B2 | 7/2009 | Christian et al. | 2003/0191497 A1 | 10/2003 | Cope | |
| 7,575,144 B2 | 8/2009 | Ortiz et al. | 2003/0195565 A1 | 10/2003 | Bonutti | |
| 7,575,548 B2 | 8/2009 | Takemoto et al. | 2003/0216611 A1 | 11/2003 | Vu | |
| 7,579,550 B2 | 8/2009 | Dayton et al. | 2003/0216615 A1 | 11/2003 | Ouchi | |
| 7,582,096 B2 | 9/2009 | Gellman et al. | 2003/0220545 A1 | 11/2003 | Ouchi | |
| 7,588,177 B2 | 9/2009 | Racenet | 2003/0225312 A1 | 12/2003 | Suzuki et al. | |
| 7,588,557 B2 | 9/2009 | Nakao | 2003/0225332 A1 | 12/2003 | Okada et al. | |
| 7,618,398 B2 | 11/2009 | Holman et al. | 2003/0229269 A1 | 12/2003 | Humphrey | |
| 7,632,250 B2 | 12/2009 | Smith et al. | 2003/0229371 A1 | 12/2003 | Whitworth | |
| 7,635,373 B2 | 12/2009 | Ortiz | 2003/0236549 A1 | 12/2003 | Bonadio et al. | |
| 7,637,903 B2 | 12/2009 | Lentz et al. | 2004/0002683 A1 | 1/2004 | Nicholson et al. | |
| 7,651,483 B2 | 1/2010 | Byrum et al. | 2004/0002735 A1 | 1/2004 | Lizardi et al. | |
| 7,651,509 B2 | 1/2010 | Bojarski et al. | 2004/0034369 A1 | 2/2004 | Sauer et al. | |
| 7,654,431 B2 | 2/2010 | Hueil et al. | 2004/0098007 A1 | 5/2004 | Heiss | |
| 7,662,089 B2 | 2/2010 | Okada et al. | 2004/0101456 A1 | 5/2004 | Kuroshima et al. | |
| 7,666,180 B2 | 2/2010 | Holsten et al. | 2004/0116948 A1 | 6/2004 | Sixto, Jr. et al. | |
| 7,674,259 B2 | 3/2010 | Shadduck | 2004/0127940 A1 | 7/2004 | Ginn et al. | |
| 7,713,189 B2 | 5/2010 | Hanke | 2004/0133077 A1 | 7/2004 | Obenchain et al. | |
| 7,713,270 B2 | 5/2010 | Suzuki | 2004/0133089 A1 | 7/2004 | Kilcoyne et al. | |
| 7,736,374 B2 | 6/2010 | Vaughan et al. | 2004/0136779 A1 | 7/2004 | Bhaskar | |
| 7,744,615 B2 | 6/2010 | Couture | 2004/0138525 A1 | 7/2004 | Saadat et al. | |
| 7,758,577 B2 | 7/2010 | Nobis et al. | 2004/0138529 A1 | 7/2004 | Wiltshire et al. | |
| 7,762,998 B2 | 7/2010 | Birk et al. | 2004/0138587 A1 | 7/2004 | Lyons, IV | |
| 7,771,416 B2 | 8/2010 | Spivey et al. | 2004/0161451 A1 | 8/2004 | Pierce et al. | |
| 7,780,683 B2 | 8/2010 | Roue et al. | 2004/0186350 A1 | 9/2004 | Brenneman et al. | |
| 7,780,691 B2 | 8/2010 | Stefanchik | 2004/0193009 A1 | 9/2004 | Jaffe et al. | |
| 7,794,409 B2 | 9/2010 | Damarati | 2004/0193146 A1 | 9/2004 | Lee et al. | |
| 7,794,475 B2 | 9/2010 | Hess et al. | 2004/0193186 A1 | 9/2004 | Kortenbach et al. | |
| 7,828,186 B2 | 11/2010 | Wales | 2004/0193188 A1 | 9/2004 | Francese | |
| 7,837,615 B2 | 11/2010 | Le et al. | 2004/0193189 A1 | 9/2004 | Kortenbach et al. | |
| 7,846,171 B2 | 12/2010 | Kullas et al. | 2004/0193200 A1 | 9/2004 | Dworschak et al. | |
| 7,850,660 B2 | 12/2010 | Uth et al. | 2004/0199052 A1 | 10/2004 | Banik et al. | |
| 7,857,183 B2 | 12/2010 | Shelton, IV | 2004/0210245 A1 | 10/2004 | Erickson et al. | |
| 7,862,546 B2 | 1/2011 | Conlon et al. | 2004/0215058 A1 | 10/2004 | Zirps et al. | |
| 7,867,216 B2 | 1/2011 | Wahr et al. | 2004/0225183 A1 | 11/2004 | Michlitsch et al. | |
| 7,892,220 B2 | 2/2011 | Faller et al. | 2004/0225186 A1 | 11/2004 | Horne, Jr. et al. | |
| 7,896,887 B2 | 3/2011 | Rimbaugh et al. | 2004/0230095 A1 | 11/2004 | Stefanchik et al. | |
| 7,909,809 B2 | 3/2011 | Scopton et al. | 2004/0230096 A1 | 11/2004 | Stefanchik et al. | |
| 7,914,513 B2 | 3/2011 | Voorhees, Jr. | 2004/0230097 A1 | 11/2004 | Stefanchik et al. | |
| 7,918,869 B2 | 4/2011 | Saadat et al. | 2004/0230161 A1 | 11/2004 | Zeiner | |
| 7,931,624 B2 | 4/2011 | Smith et al. | 2004/0249246 A1 | 12/2004 | Campos | |
| 7,945,332 B2 | 5/2011 | Schechter | 2004/0249367 A1 | 12/2004 | Saadat et al. | |
| 7,947,000 B2 | 5/2011 | Vargas et al. | 2004/0249394 A1 | 12/2004 | Morris et al. | |
| 7,955,298 B2 | 6/2011 | Carroll et al. | 2004/0249443 A1 | 12/2004 | Shanley et al. | |
| 7,963,975 B2 | 6/2011 | Criscuolo | 2005/0004515 A1 | 1/2005 | Hart et al. | |
| 7,988,685 B2 | 8/2011 | Ziaie et al. | 2005/0033265 A1 | 2/2005 | Engel et al. | |
| 8,075,587 B2 | 12/2011 | Ginn | 2005/0033277 A1 | 2/2005 | Clague et al. | |
| 2001/0049497 A1 | 12/2001 | Kalloo et al. | 2005/0033319 A1 | 2/2005 | Gambale et al. | |

| | | |
|---|---|---|
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247576 A1 | 11/2006 | Poncet |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |

| | | |
|---|---|---|
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287206 A1 | 11/2009 | Jun |
| 2009/0287236 A1 | 11/2009 | Bakos et al. |

| | | | | | | |
|---|---|---|---|---|---|---|
| 2009/0292164 A1 | 11/2009 | Yamatani | EP | 0589454 A2 | 3/1994 | |
| 2009/0299135 A1 | 12/2009 | Spivey | EP | 0464479 B1 | 3/1995 | |
| 2009/0299143 A1 | 12/2009 | Conlon et al. | EP | 0529675 B1 | 2/1996 | |
| 2009/0299362 A1 | 12/2009 | Long et al. | EP | 0724863 B1 | 7/1999 | |
| 2009/0299385 A1 | 12/2009 | Stefanchik et al. | EP | 0760629 B1 | 11/1999 | |
| 2009/0299406 A1 | 12/2009 | Swain et al. | EP | 0818974 B1 | 7/2001 | |
| 2009/0299409 A1 | 12/2009 | Coe et al. | EP | 1281356 A2 | 2/2003 | |
| 2009/0306658 A1 | 12/2009 | Nobis et al. | EP | 0947166 B1 | 5/2003 | |
| 2009/0306683 A1 | 12/2009 | Zwolinski et al. | EP | 0836832 B1 | 12/2003 | |
| 2009/0322864 A1 | 12/2009 | Karasawa et al. | EP | 1402837 A1 | 3/2004 | |
| 2009/0326561 A1 | 12/2009 | Carroll, II et al. | EP | 0744918 B1 | 4/2004 | |
| 2010/0010294 A1 | 1/2010 | Conlon et al. | EP | 0931515 B1 | 8/2004 | |
| 2010/0010298 A1 | 1/2010 | Bakos et al. | EP | 0941128 B1 | 10/2004 | |
| 2010/0010299 A1 | 1/2010 | Bakos et al. | EP | 1411843 B1 | 10/2004 | |
| 2010/0010303 A1 | 1/2010 | Bakos | EP | 1150614 B1 | 11/2004 | |
| 2010/0010510 A1 | 1/2010 | Stefanchik | EP | 1477104 A1 | 11/2004 | |
| 2010/0010511 A1 | 1/2010 | Harris et al. | EP | 1481642 A1 | 12/2004 | |
| 2010/0023032 A1 | 1/2010 | Granja Filho | EP | 1493391 A1 | 1/2005 | |
| 2010/0036198 A1 | 2/2010 | Tacchino et al. | EP | 0848598 B1 | 2/2005 | |
| 2010/0042045 A1 | 2/2010 | Spivey | EP | 1281360 B1 | 3/2005 | |
| 2010/0048990 A1 | 2/2010 | Bakos | EP | 1568330 A1 | 8/2005 | |
| 2010/0049223 A1 | 2/2010 | Granja Filho | EP | 1452143 B1 | 9/2005 | |
| 2010/0056861 A1 | 3/2010 | Spivey | EP | 1616527 A2 | 1/2006 | |
| 2010/0056862 A1 | 3/2010 | Bakos | EP | 1006888 B1 | 3/2006 | |
| 2010/0057085 A1 | 3/2010 | Holcomb et al. | EP | 1629764 A1 | 3/2006 | |
| 2010/0057108 A1 | 3/2010 | Spivey et al. | EP | 1013229 B1 | 6/2006 | |
| 2010/0063538 A1 | 3/2010 | Spivey et al. | EP | 1721561 A1 | 11/2006 | |
| 2010/0076451 A1 | 3/2010 | Zwolinski et al. | EP | 1153578 B1 | 3/2007 | |
| 2010/0081877 A1 | 4/2010 | Vakharia | EP | 1334696 B1 | 3/2007 | |
| 2010/0087813 A1 | 4/2010 | Long | EP | 1769766 A1 | 4/2007 | |
| 2010/0113872 A1 | 5/2010 | Asada et al. | EP | 1836971 A2 | 9/2007 | |
| 2010/0121362 A1 | 5/2010 | Clague et al. | EP | 1836980 A1 | 9/2007 | |
| 2010/0130817 A1 | 5/2010 | Conlon | EP | 1854421 A2 | 11/2007 | |
| 2010/0130975 A1 | 5/2010 | Long | EP | 1857061 A1 | 11/2007 | |
| 2010/0131005 A1 | 5/2010 | Conlon | EP | 1875876 A1 | 1/2008 | |
| 2010/0152539 A1 | 6/2010 | Ghabrial et al. | EP | 1891881 A1 | 2/2008 | |
| 2010/0152609 A1 | 6/2010 | Zwolinski et al. | EP | 1902663 A1 | 3/2008 | |
| 2010/0152746 A1 | 6/2010 | Ceniccola et al. | EP | 1477106 B1 | 6/2008 | |
| 2010/0179510 A1 | 7/2010 | Fox et al. | EP | 1949844 A1 | 7/2008 | |
| 2010/0179530 A1 | 7/2010 | Long et al. | EP | 1518499 B1 | 8/2008 | |
| 2010/0191050 A1 | 7/2010 | Zwolinski | EP | 1709918 B1 | 10/2008 | |
| 2010/0191267 A1 | 7/2010 | Fox | EP | 1985226 A2 | 10/2008 | |
| 2010/0198005 A1 | 8/2010 | Fox | EP | 1994904 A1 | 11/2008 | |
| 2010/0198149 A1 | 8/2010 | Fox | EP | 1707130 B1 | 12/2008 | |
| 2010/0198244 A1 | 8/2010 | Spivey et al. | EP | 0723462 B1 | 3/2009 | |
| 2010/0198248 A1 | 8/2010 | Vakharia | EP | 1769749 B1 | 11/2009 | |
| 2010/0249700 A1 | 9/2010 | Spivey | EP | 1493397 B1 | 9/2011 | |
| 2010/0286791 A1 | 11/2010 | Goldsmith | FR | 2731610 A1 | 9/1996 | |
| 2010/0298642 A1 | 11/2010 | Trusty et al. | GB | 330629 A | 6/1930 | |
| 2010/0312056 A1 | 12/2010 | Galperin et al. | GB | 2335860 A | 10/1999 | |
| 2010/0331622 A2 | 12/2010 | Conlon | GB | 2403909 A | 1/2005 | |
| 2010/0331774 A2 | 12/2010 | Spivey | GB | 2421190 A | 6/2006 | |
| 2011/0093009 A1 | 4/2011 | Fox | GB | 2443261 A | 4/2008 | |
| 2011/0098694 A1 | 4/2011 | Long | JP | 56-46674 | 4/1981 | |
| 2011/0098704 A1 | 4/2011 | Long et al. | JP | 63309252 A | 12/1988 | |
| 2011/0105850 A1 | 5/2011 | Voegele et al. | JP | 4038960 A | 2/1992 | |
| 2011/0112434 A1 | 5/2011 | Ghabrial et al. | JP | 8-29699 A | 2/1996 | |
| 2011/0115891 A1 | 5/2011 | Trusty | JP | 2002-369791 A | 12/2002 | |
| 2011/0124964 A1 | 5/2011 | Nobis | JP | 2003-088494 A | 3/2003 | |
| 2011/0152609 A1 | 6/2011 | Trusty et al. | JP | 2003-235852 A | 8/2003 | |
| 2011/0152610 A1 | 6/2011 | Trusty et al. | JP | 2004-33525 A | 2/2004 | |
| 2011/0152612 A1 | 6/2011 | Trusty et al. | JP | 2004-065745 A | 3/2004 | |
| 2011/0152858 A1 | 6/2011 | Long et al. | JP | 2005-121947 A | 5/2005 | |
| 2011/0152859 A1 | 6/2011 | Long et al. | JP | 2005-261514 A | 9/2005 | |
| 2011/0152878 A1 | 6/2011 | Trusty et al. | JP | 2006297005 A | 11/2006 | |
| 2011/0152923 A1 | 6/2011 | Fox | NL | 1021295 C2 | 2/2004 | |
| 2011/0160514 A1 | 6/2011 | Long et al. | SU | 194230 | 5/1967 | |
| 2011/0190659 A1 | 8/2011 | Long et al. | SU | 980703 | 12/1982 | |
| 2011/0190764 A1 | 8/2011 | Long et al. | WO | WO 84/01707 A1 | 5/1984 | |
| 2011/0245619 A1 | 10/2011 | Holcomb | WO | WO 92/13494 A1 | 8/1992 | |
| 2011/0306971 A1 | 12/2011 | Long | WO | WO 93/10850 A1 | 6/1993 | |
| | | | WO | WO 93/20760 A1 | 10/1993 | |
| FOREIGN PATENT DOCUMENTS | | | WO | WO 93/20765 A1 | 10/1993 | |
| DE | 4323585 A1 | 1/1995 | WO | WO 95/09666 A1 | 4/1995 | |
| DE | 19713797 A1 | 10/1997 | WO | WO 96/22056 A1 | 7/1996 | |
| DE | 19757056 B4 | 8/2008 | WO | WO 96/27331 A1 | 9/1996 | |
| DE | 102006027873 B4 | 10/2009 | WO | WO 96/39946 A1 | 12/1996 | |
| EP | 0086338 A1 | 8/1983 | WO | WO 97/12557 A1 | 4/1997 | |
| EP | 0286415 A2 | 10/1988 | WO | WO 98/01080 A1 | 1/1998 | |

| | | |
|---|---|---|
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/012630 A1 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

Zadno et al., "Linear Superelasticity in Cold-Worked NI-TI," Engineering Aspects of Shape Memory Alloys, pp. 414-419 (1990).
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
International Search Report for PCT/US2009/054453, Mar. 23, 2010 (8 pages).
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve,"Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du Feb. 24, 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.

B. Rubinsky, Ph.D., "Irreversible Electroporation in Medicine," Technology in Cancer Research and Treatment, vol. 6, No. 4, Aug. (2007), pp. 255-259.

How Stuff Works "How Smart Structures Will Work," http://science.howstuffworks.com/engineering/structural/smart-structure1.htm; accessed online Nov. 1, 2011 (3 pages).

Instant Armor: Science Videos—Science News—ScienCentral; http://www.sciencentral.com/articles./view.php3?article_id=218392121; accessed online Nov. 1, 2011 (2 pages).

Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).

Jolly et al., Properties and Applications of Commercial Magnetorheological Fluids. SPIE 5th Annual Int. Symposium on Smart Structures and Materials, 1998 (18 pages).

U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.

Partial International Search Report for PCT/US2009/054453, Dec. 10, 2009 (2 pages).

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&nav-RelId=1000.1003&method=D..., accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNAa delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

Hakko Retractors, obtained Aug. 25, 2009 (5 pages).

U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/694,452, filed Jan. 27, 2010.
U.S. Appl. No. 12/752,701, filed Apr. 1, 2010.

* cited by examiner

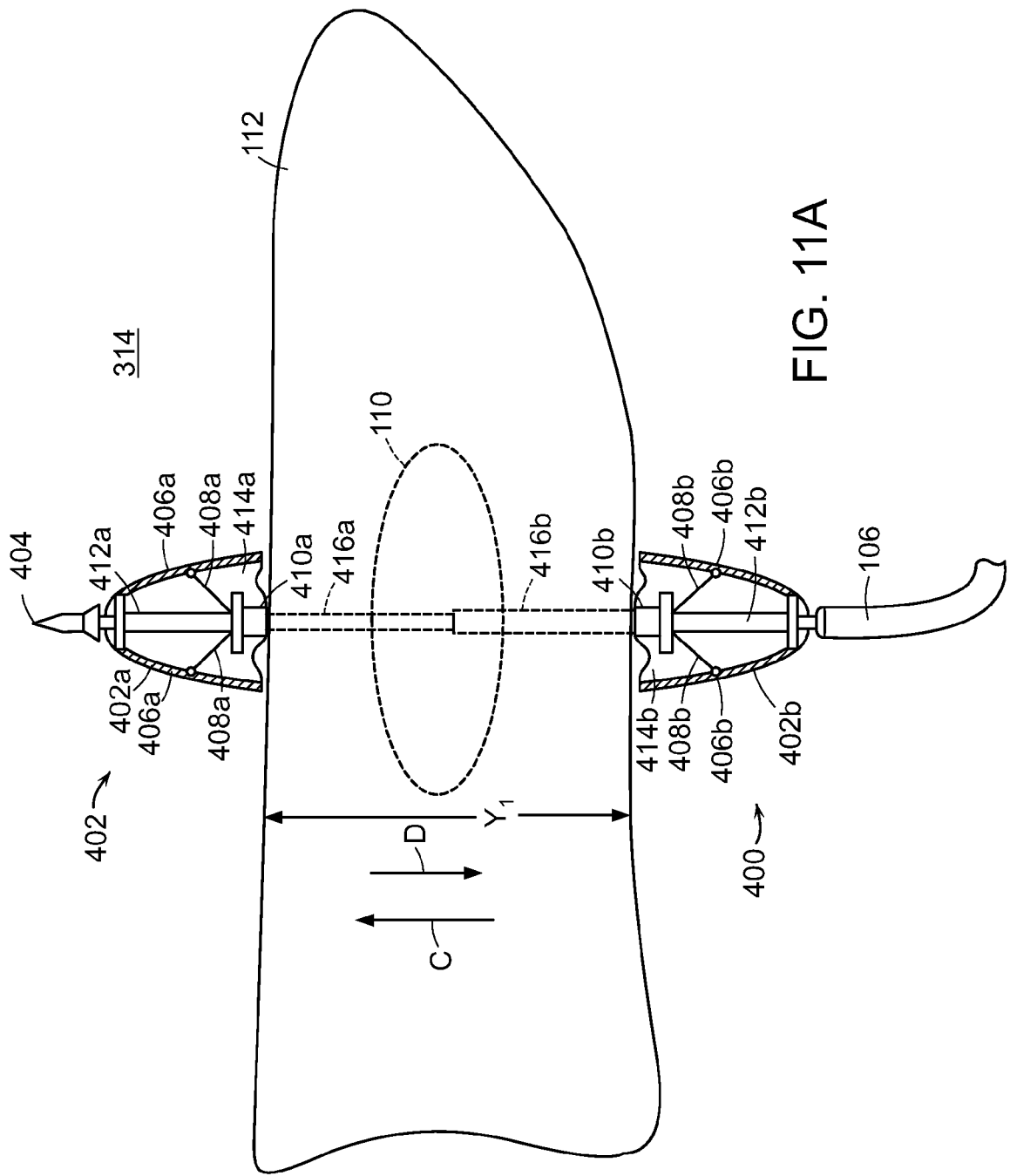

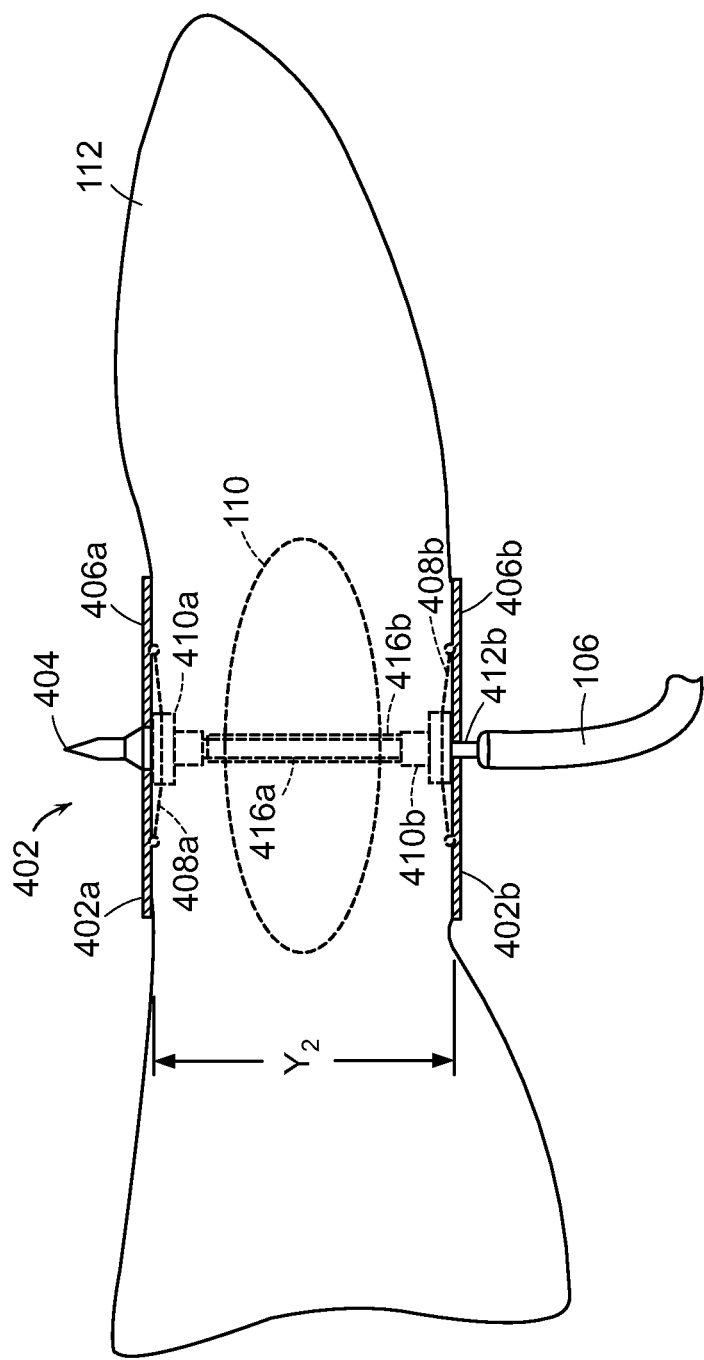
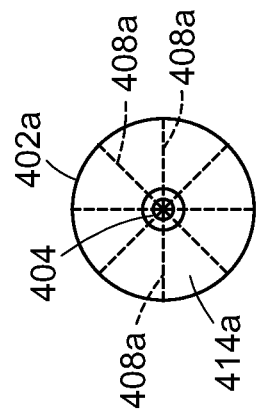
FIG. 11C
FIG. 11D

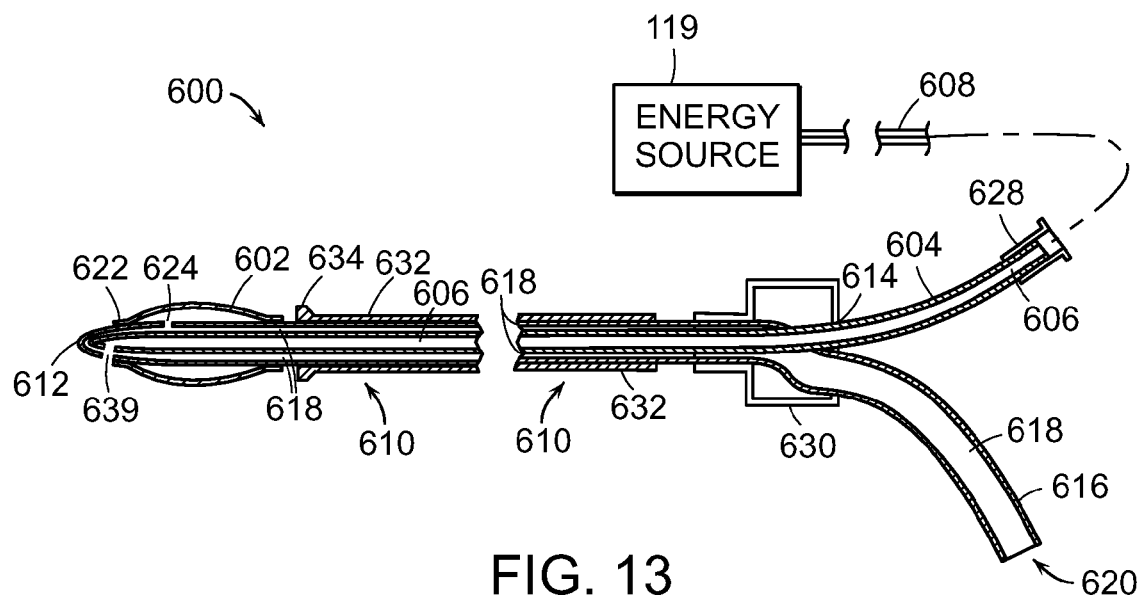
FIG. 13
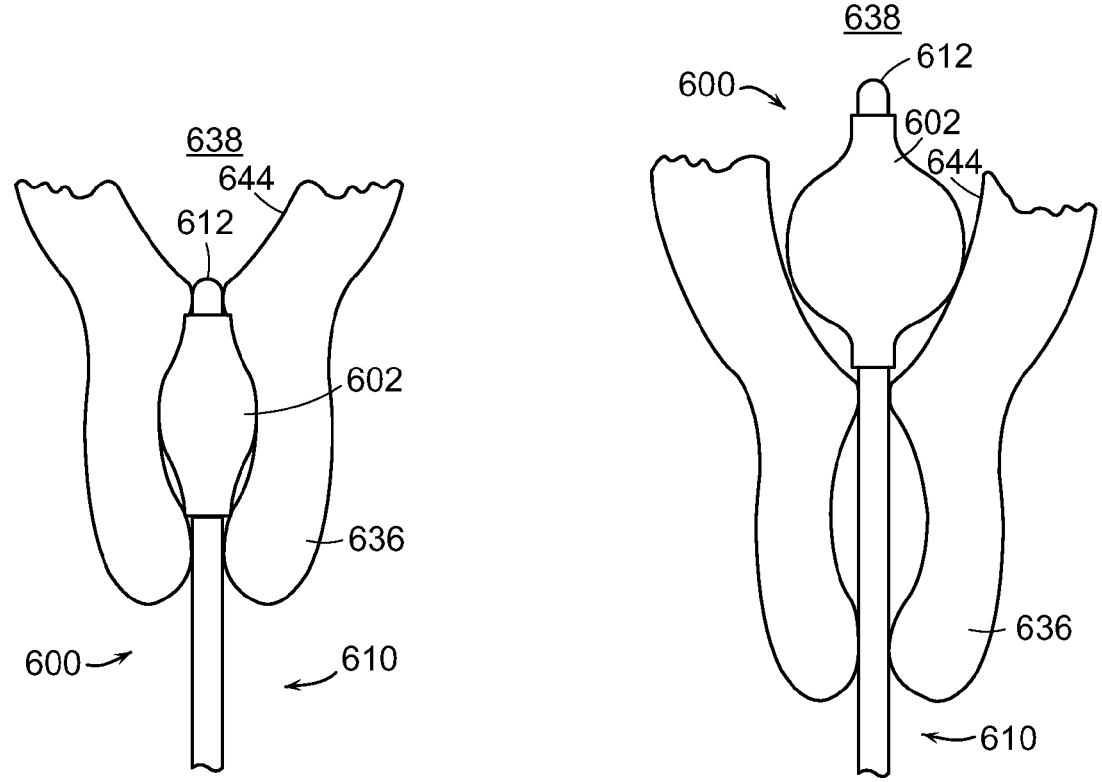
FIG. 14A
FIG. 14B

ELECTRICAL ABLATION DEVICES

BACKGROUND

Electrical ablation has been employed in medicine for the removal and treatment of a variety of abnormal tissues or growths, such as cancers or tumors. Electrical ablation may be used to treat benign prostatic hyperplasia (BPH), restricted gastric tissue, menorrhagia, and to remove adipose tissue. Other uses include removal of excess skin following bariatric surgery. Tumors in solid organs, such as the liver or lungs, may be treated or destroyed using electric direct current (DC) pulses. The abnormal tissue may be removed or treated with energy delivered by electrodes attached to therapy probes. The electrodes are positioned proximate or in contact with the diseased tissue and then energized by a variety of energy sources.

Menorrhagia is a medical condition that describes heavy and prolonged menstrual bleeding. While there are many potential causes for menorrhagia, the most common include hormone (estrogen and progesterone) imbalance, pelvic inflammatory disease, uterine fibroids, and infection. Current treatments for menorrhagia include iron supplements, prostaglandin inhibitors, oral contraceptives, and in severe cases—endometrial ablation and hysterectomy. Endometrial ablation involves introducing a conforming bipolar electrode into the uterine cavity, insufflation of the uterine cavity with $CO_2$ (to check for cavity integrity), and then application of bipolar RF energy to the uterine wall for 90 seconds or more. An alternative to RF ablation is ultrasonic ablation.

Bariatric surgery remains a popular and successful option to assist morbidly obese patients. The procedure substantially reduces the patient's body mass index and resolves many associated comorbidities of obesity. One of the potential problems associated with bariatric surgery is the excess skin remaining after the patient has lost substantial weight. The effects of bariatric surgery occur so quickly and with such an impact that the body loses weight at a much faster rate than it can reduce the excess skin previously needed for the larger body. Many patients who are self-conscious of their appearance will consult with cosmetic surgeons following the bariatric procedure to investigate options for having the excess skin surgically removed.

While current methods and devices used in electrical ablation are effective, one drawback with conventional electrical ablation therapy is the resulting permanent damage that may occur to the tissue. This may be particularly true with uterine tissue, where conventional ablation therapy could cause permanent damage and potentially may result in complications with becoming pregnant. Other drawbacks of conventional ablation therapy are cost, lengthy recovery periods, and it can be extraordinarily painful.

Accordingly, there remains a need for improved electrical ablation methods and devices. There is also a need to provide improved electrical ablation therapies over time.

FIGURES

The novel features of the various embodiments are set forth with particularity in the appended claims. The various embodiments, however, both as to organization and methods of operation, together with the advantages thereof, may be understood by reference to the following description taken in conjunction with the accompanying drawings as follows:

FIG. 11A illustrates one embodiment of an electrical ablation device being deployed through a tumor and a liver.

FIG. 11C illustrates a liver slightly compressed by the first and second electrodes of the electrical ablation device in FIG. 11A.

FIG. 11D is a top-view of one embodiment of the first electrode of the electrical ablation device in FIG. 11A shown in an open position.

FIG. 13 illustrates one embodiment of an electrical ablation device.

FIG. 14A illustrates a balloon electrode of the electrical ablation device shown in FIG. 13 in a deflated state inserted into the cervix.

FIG. 14B illustrates the balloon electrode shown in FIG. 14A inserted in the uterine cavity in a partially inflated state.

DESCRIPTION

Figure 1:
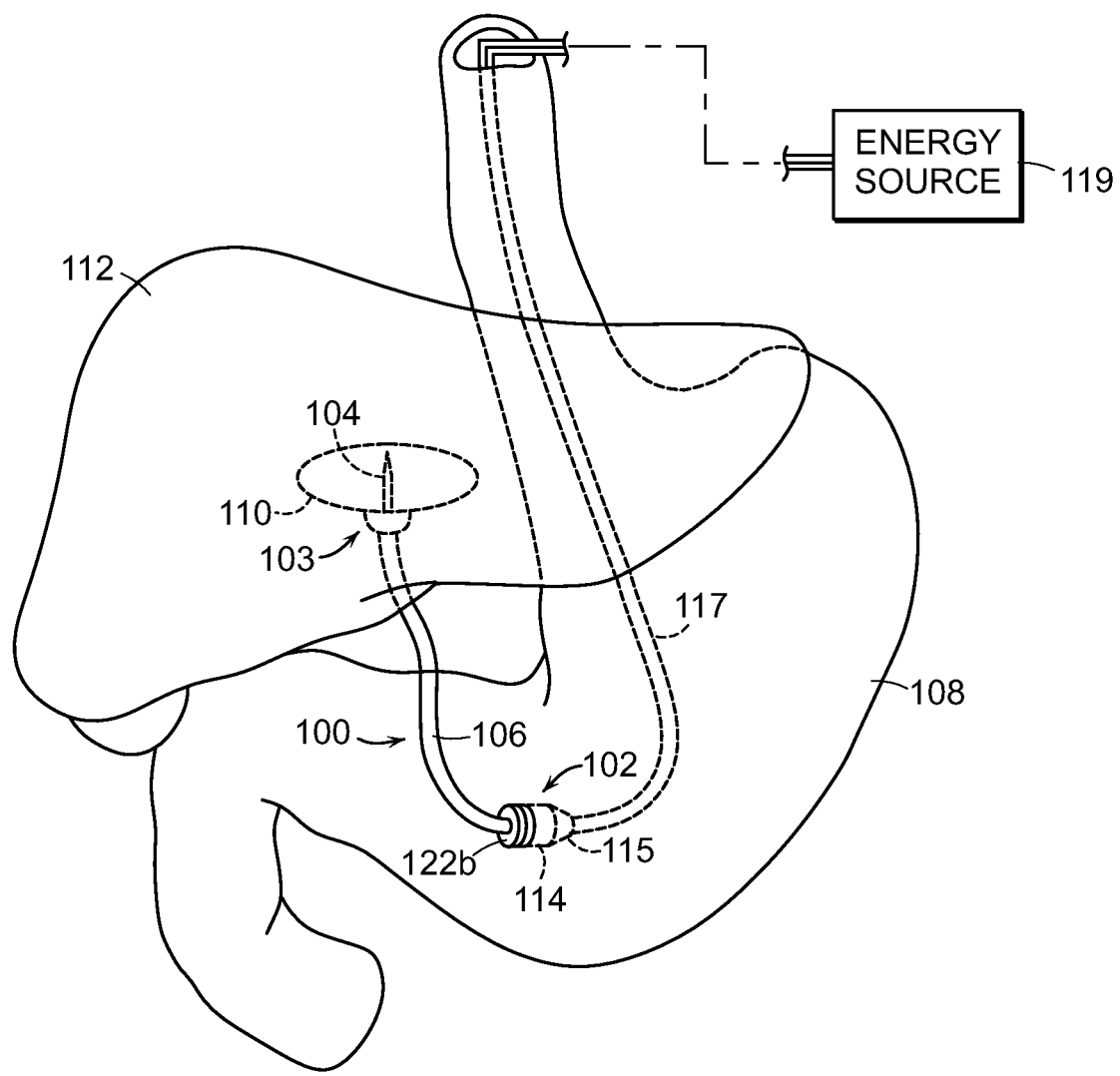
FIG. 1 illustrates one embodiment of an electrical ablation device shown in use.

Various embodiments are described to provide an overall understanding of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined, in whole or in part, with the features of other embodiments. Such modifications and variations are intended to be included within the scope of the claims.

It will be appreciated that the terms "proximal" and "distal" are used herein with reference to a clinician manipulating one end of an instrument that protrudes out of a natural orifice (or opening) of the patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the drawings. However, surgical instruments may be used in many orientations and positions, and these terms are not intended to be limiting and absolute.

The electrical ablation devices comprise electrodes that can be positioned inside a patient proximal to a treatment region (e.g., target site or worksite) where there is evidence of abnormal tissue growth. The electrodes comprise an electrically conductive portion (e.g., medical grade stainless steel) and are coupled to an energy source. Once the electrodes are positioned proximal to the treatment region, an energizing potential is applied to the electrodes to deliver electric current to the treatment region to remove the abnormal tissue. The electric current is supplied by an external energy source having a control unit or generator. The energizing potential (and the resulting electric current) may be characterized by a particular waveform in terms of frequency, amplitude, pulse width, and polarity. Depending on the diagnostic or therapeutic treatment to be rendered, the electrode may be configured as either an anode (−) or a cathode (−) or may comprise a plurality of electrodes with at least one configured as an anode (+) and the at least one another one configured as the cathode (−). Regardless of the initial configuration, the polarity of the electrodes may be reversed by reversing the polarity of the output of the energy source.

The energy source generates an electric field having a suitable characteristic waveform output in terms of frequency, amplitude, pulse width, and polarity. Depending on the diagnostic or therapeutic treatment to be rendered, the therapy probes may comprise one electrode containing both a cathode and an anode or may contain a plurality of electrodes with at least one serving as a cathode and at least one serving as an anode. The electrodes may be energized with DC voltages and conduct currents at various frequencies, amplitudes, pulse widths, and polarities. The electrodes also may be energized with time-varying voltages and currents at amplitudes and frequencies suitable for rendering the desired therapy. A suitable energy source may comprise an electrical waveform generator adapted to deliver DC and/or time-varying energizing potentials characterized by frequency, amplitude, pulse width, and/or polarity to the electrodes. The electric current flows between the electrodes and through the diseased tissue proportionally to the potential (e.g., voltage) applied to the electrodes. In one embodiment, the energy source may comprise a wireless transmitter to deliver energy to the electrodes via one or more antennas.

The various embodiments of the electrical ablation devices described hereinbelow utilize electroporation or electropermeabilization techniques to apply external electric fields (electric potentials) to cell membranes to significantly increase the electrical conductivity and permeability of the plasma in the cell membranes. Irreversible electroporation (IRE) is the process of killing cells by applying large destabilizing electrical potentials across the cell membranes for a long period of time. IRE provides an effective method for destroying cells while avoiding some of the negative complications of heat-inducing therapies. Namely, IRE destroys cells without the use of heat and does not destroy cellular support structure or regional vasculature. Large destabilizing IRE electric potentials may be in the range of about several hundred to about several thousand volts applied across biological membranes over a distance of about several millimeters, for example, for a relatively long period of time. The destabilizing electric potential forms pores in the cell membrane when the potential across the cell membrane exceeds its dielectric strength causing the cell to die by processes known as apoptosis and/or necrosis. Embodiments of the electrical therapy devices may be employed in the treatment of cancer by destroying live abnormal (e.g., cancerous) tissue in-vivo through the delivery of destabilizing electric potential energy to diseased tissue to quickly create cell necrosis and ablation in the cells of tumors, masses, lesions, and other abnormal growths.

FIG. 1 illustrates one embodiment of an electrical ablation device 100 shown in use. In one embodiment, the electrical ablation device 100 may be used in treatment of abnormal tissues or growths, such as cancers or tumors, formed in or on solid organs, BPH, and restricted gastric tissue using IRE energy. In other embodiments, electrical ablation treatment may be applied using other forms of electrical energy, such as those described herein. In the illustrated embodiment, the electrical ablation device 100 is shown disposed between a hollow body lumen and a solid organ. In one embodiment, the electrical ablation device 100 comprises a proximal end 102 configured for attachment through the wall of a hollow body lumen and a distal end 103 configured for attachment to abnormal tissues or growths, such as cancers or tumors, formed in a solid organ. The proximal end 102 may be attached to tissue that is endoscopically, laparoscopically, percutaneously, or transcutaneously accessible. In one embodiment, the proximal end 102 may be attached through a hollow body lumen that is endoscopically, laparoscopically, percutaneously, or transcutaneously accessible. Examples of a hollow body lumen include, for example, the esophagus, the stomach, the intestines, the colon, and may include the peritoneal cavity. In one embodiment, the proximal end 102 may be attached through the body percutaneously or transcutaneously—through the patient's skin—such that the proximal end 102 may be coupled to the energy source 119 externally and the electrical ablation device 100 may be energized from outside the patient's body. In the embodiment illustrated in FIG. 1, the electrical ablation device 100 is disposed between the stomach 108 and the liver 112. The proximal end 102 is disposed through the stomach 108 and the distal end 103 is disposed through a tumor 110 formed in the liver 112. An electrode 104 at the distal end 103 is positioned through the liver 112 and the tumor 110. The proximal end 102 of the electrical ablation device 100 may be attached to the wall 118 (FIG. 2) of the stomach 108 and the distal end 103 of the electrical ablation device 100 may be attached to the liver 112.

Figure 2:
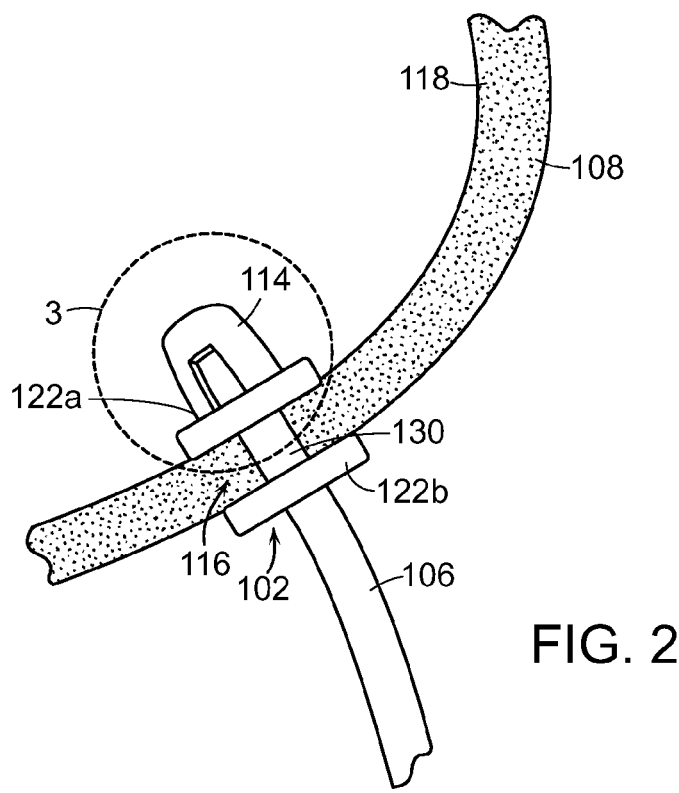
FIG. 2 is a partial cross-sectional view of a wall of a hollow body lumen comprising the proximal end of the electrical ablation device in FIG. 1 attached therethrough.

FIG. 2 is a partial cross-sectional view of a wall 118 of a hollow body lumen comprising the proximal end 102 of the electrical ablation device 100 attached therethrough. In the embodiment illustrated in FIG. 2, the proximal end 102 of the electrical ablation device 100 is attached through the wall 118 of the stomach 108. Referring to FIGS. 1 and 2, the proximal end 102 of the electrical ablation device 100 comprises a connector 114 and a fastener 116, which is inserted through the wall 118 of the stomach 108 and is secured thereto. In one embodiment, the connector 114 and the fastener 116 may be inserted through the body percutaneously or transcutaneously. For example, the connector 114 and the fastener 116 may be inserted through the abdominal wall and may be secured thereto. The connector 114 may be formed as a semi-permanent port. The fastener 116 comprises first and second flanges 122a, 122b connected by a hollow shaft 130 defining a longitudinal opening. The flanges 122a, b provide for the transmural attachment of the connector 114 through the wall 118 of the stomach 108 and seal the opening through the wall 118 of the stomach 108 where the shaft 130 is received. A first cable 106 is received through the longitudinal opening in the shaft 130. The cable 106 may comprise one or more electrically conductive wires electrically coupled to the connector 114 to provide electrical communication through the wall 118 of the stomach 108. In the embodiment illustrated in FIG. 1, the connector 114 is coupled to a corresponding mating female plug 115 located inside the stomach 108. The plug 115 is coupled to an energy source 119 via a second cable 117, which also may comprise one or more electrically conductive wires. The cable 117 may be introduced into the stomach 108 through the access channel or working channel of a flexible endoscope, an overtube, or though a small—keyhole—incision in the abdomen.

Figure 19:
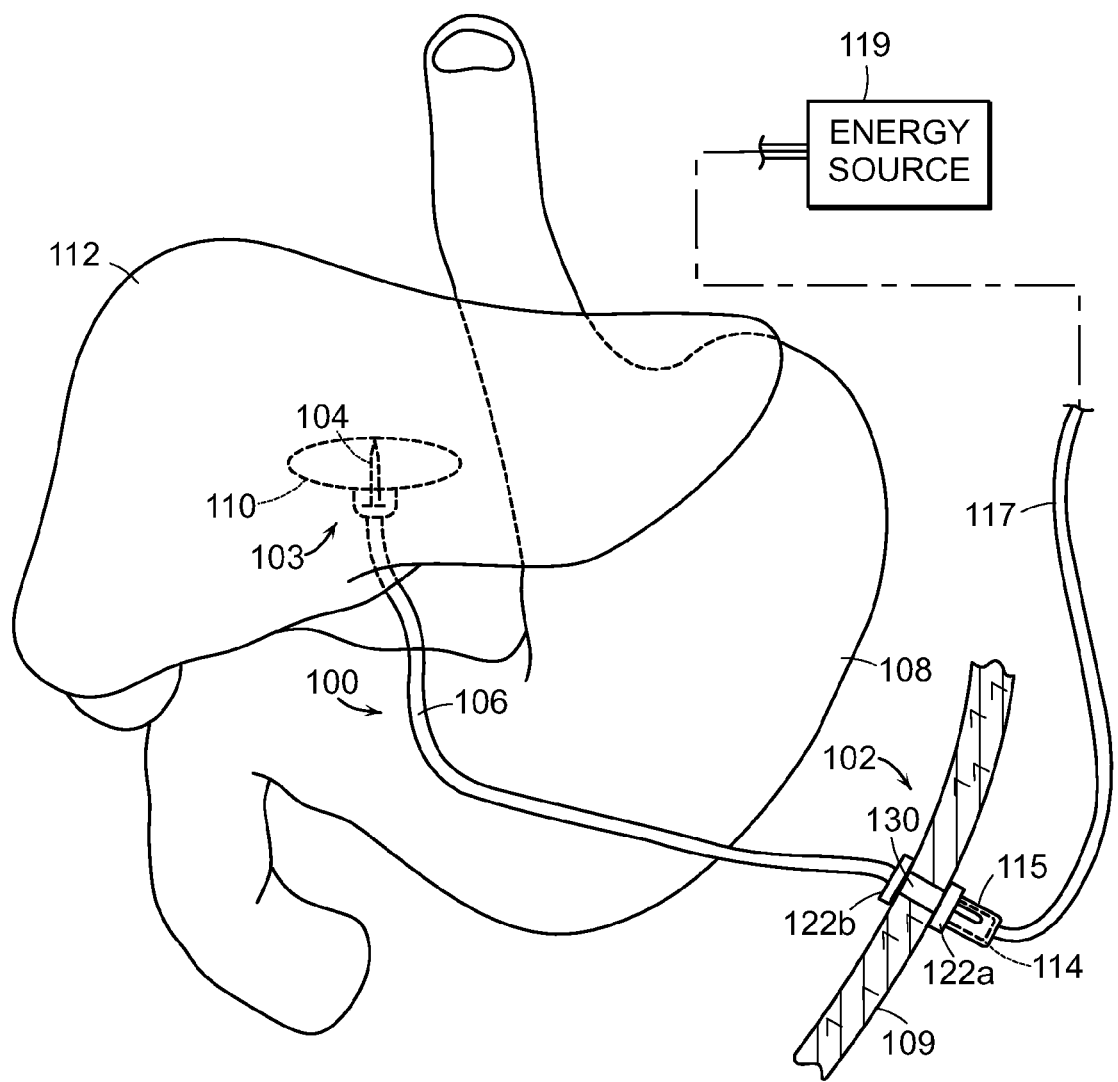
FIG. 19 illustrates one embodiment of an electrical ablation device shown in use percutaneously, through the patient's skin.

FIG. 19 illustrates one embodiment of the electrical ablation device 100 shown in use percutaneously, through the patient's skin. In one embodiment, the connector 114 and the fastener 116 are inserted through the body percutaneously or transcutaneously. As illustrated in FIG. 19, for example, the connector 114 and the fastener 116 are be inserted through the abdominal wall 109 and may be secured thereto with the first and second flanges 122a, 122b connected by the hollow shaft 130. The flanges 122a, b provide for the transmural attachment of the connector 114 through the abdominal wall 109 and seal the opening where the shaft 130 is received. The plug 115 is coupled to the connector 114 one end and to the energy source 119 on another end by the second cable 117, which also may comprise one or more electrically conductive wires.

Referring back to FIGS. 1 and 2, in one embodiment, the connector 114 may be attached to the wall 118 of the stomach 108 using a variety of fasteners. The connector 114 opens to the inside of the stomach 108 and the fastener 116 is used to attach the connector 114 to the wall 118 of the stomach 108. The energy source 119 is coupled to the connector 114 via the plug 115. Electrical energy generated by the energy source 119 are communicated by the cable 117 and the connector 114 through the wall 118 of the stomach 108. The electrical energy is communicated by the cable 106 to the electrode 104. As described in more detail with reference to FIG. 20, in one embodiment the electrical energy is communicated to the electrode 104 wirelessly by way of one or more antennas.

Referring to FIG. 1, in one embodiment, the electrode 104 may be attached to the tumor 110 and/or the liver 112 using a variety of fasteners. The electrode 104 is located approximately in the center of the tumor 110. In one embodiment, the electrode 104 may be configured as an anode (+) coupled to a positive terminal of the energy source 119. A second electrode may be configured as a cathode (−) coupled to a negative terminal of the energy source 119 to form a conductive return path or surface and may be located in the stomach 108 or elsewhere. It will be appreciated that the electrode 104 may be configured either as the anode (+) or the cathode (−) and the polarity of the electrode 104 may be reversed by reversing the output of the energy source 119. In one embodiment, the second electrode may be an electrically conductive balloon (not shown) located in the stomach 108 or other internal body lumen. The first and second electrodes may be inserted inside the patient's body using laparoscopic or endoscopic minimally invasive surgical techniques.

Figure 3:
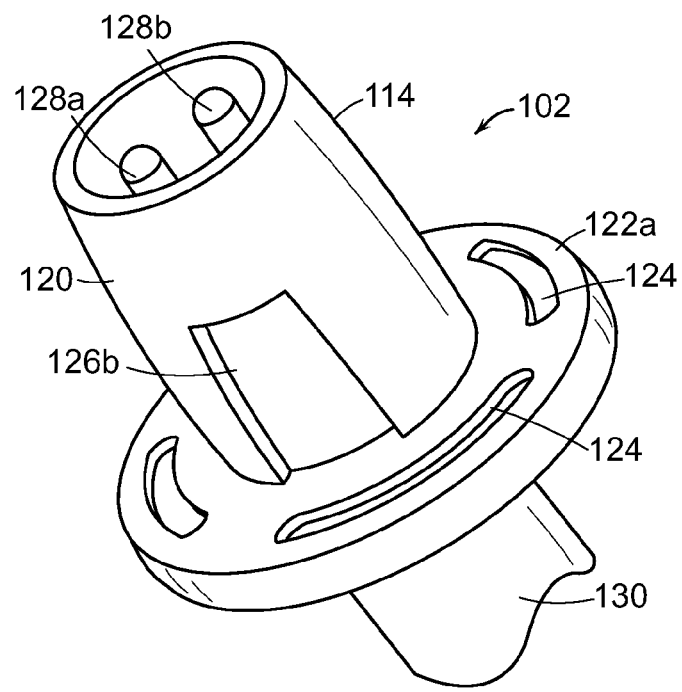
FIG. 3 illustrates one embodiment of a connector configured for attachment through the wall of a hollow body lumen.

FIG. 3 illustrates one embodiment of the connector 114 configured for attachment through the wall 118 of a hollow body lumen. In the embodiment illustrated in FIG. 3, the connector 114 comprises a body 120 and the flange 122a. In one embodiment, the first flange 122a comprises one or more openings 124 for receiving sutures or tags for attaching the connector 114 to the wall 118 of the stomach 108 (both shown in FIG. 2). Although not shown in FIG. 3, the second flange 122b may comprise similar openings for receiving sutures or tags for attaching the connector 114 to the wall 118 of the stomach 108. The connector 114 comprises one or more terminals 128a, 128b, for example, to receive a corresponding female plug (e.g., plug 115 shown in FIG. 1) configured to connect to the first and second terminals 128a, 128b. First ends of the one or more electrically conductive wires disposed in the cable 106 are connected to the one or more terminals 128a, b. The body 120 also includes a first and second recesses 126a, 126b (126b not shown) for receiving corresponding tabs formed on a mating female plug portion configured to electrically coupled to the connector 114. The body is formed of an electrically insulative material such as medical grade polyester, for example, to electrically isolate the one or more terminals 128a, b from the wall 118 of the stomach 108.

Figure 4:
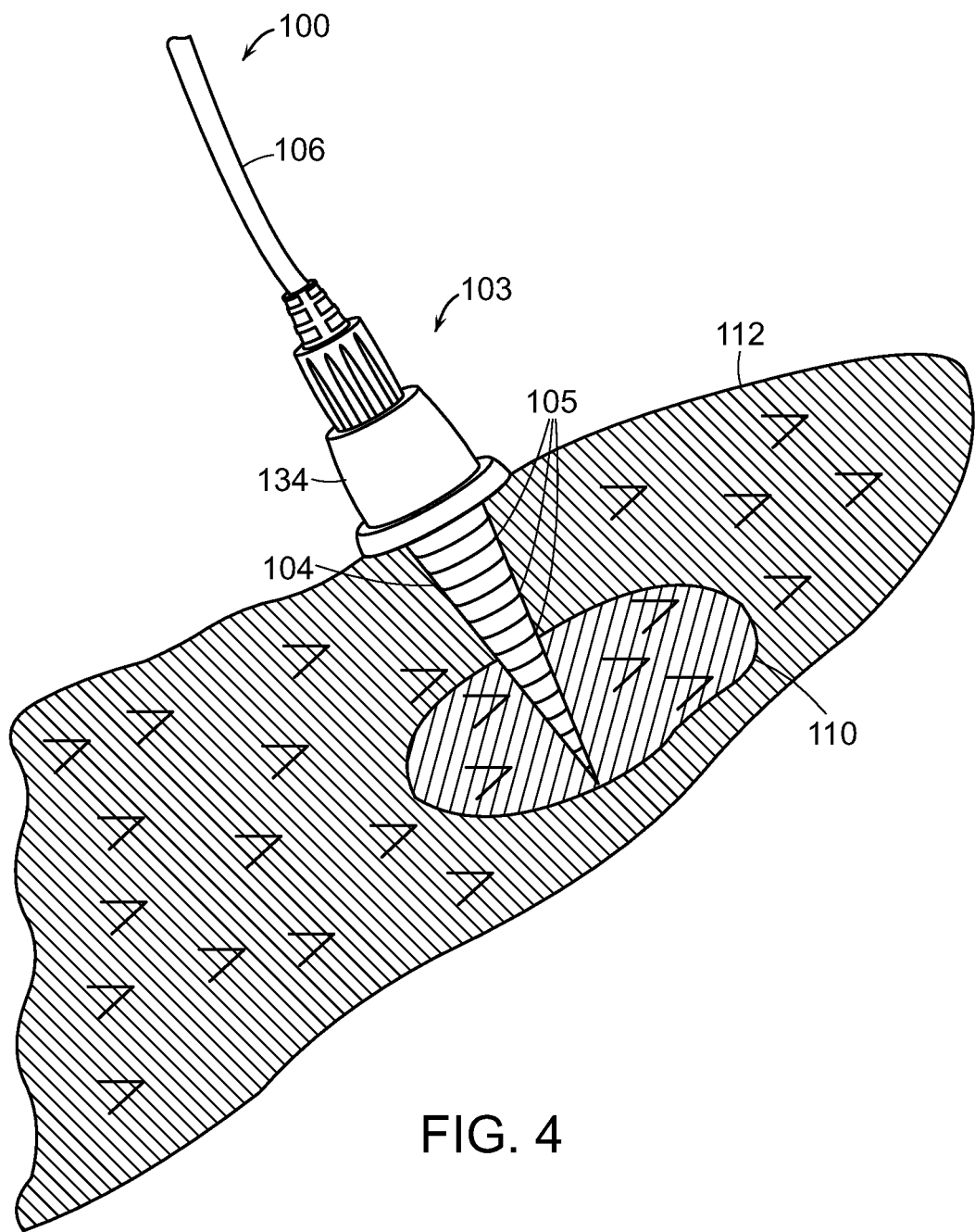
FIG. 4 is a cross-sectional view of one embodiment of the electrical ablation device in FIG. 1 shown in use in treatment of abnormal tissues or growths, such as cancers or tumors, formed in solid organs.

FIG. 4 is a cross-sectional view of one embodiment of the electrical ablation device 100 shown in use in treatment of abnormal tissues or growths, such as cancers or tumors, formed in solid organs. In the embodiment illustrated in FIG. 4, the electrode 104 is embedded into the tumor 110 formed in the liver 112. The distal end 103 of the electrical ablation device 100 comprises a connector 134 adapted to couple to the cable 106. The electrode 104 is adapted to embed into the liver 112 and the tumor 110. The electrode 104 comprises a tapered body for easy insertion into solid body organs. In one embodiment, the electrode 104 may be formed in the shape of a needle electrode. Ridges 105 may be formed on an outer surface of the tapered body of the electrode 104 to allow for penetration attachment of the electrode 104 to tissue. The electrode 104 comprises at least one electrically conductive portion that is formed of or coated with an electrically conductive material such as medical grade stainless steel, for example.

Figure 5:
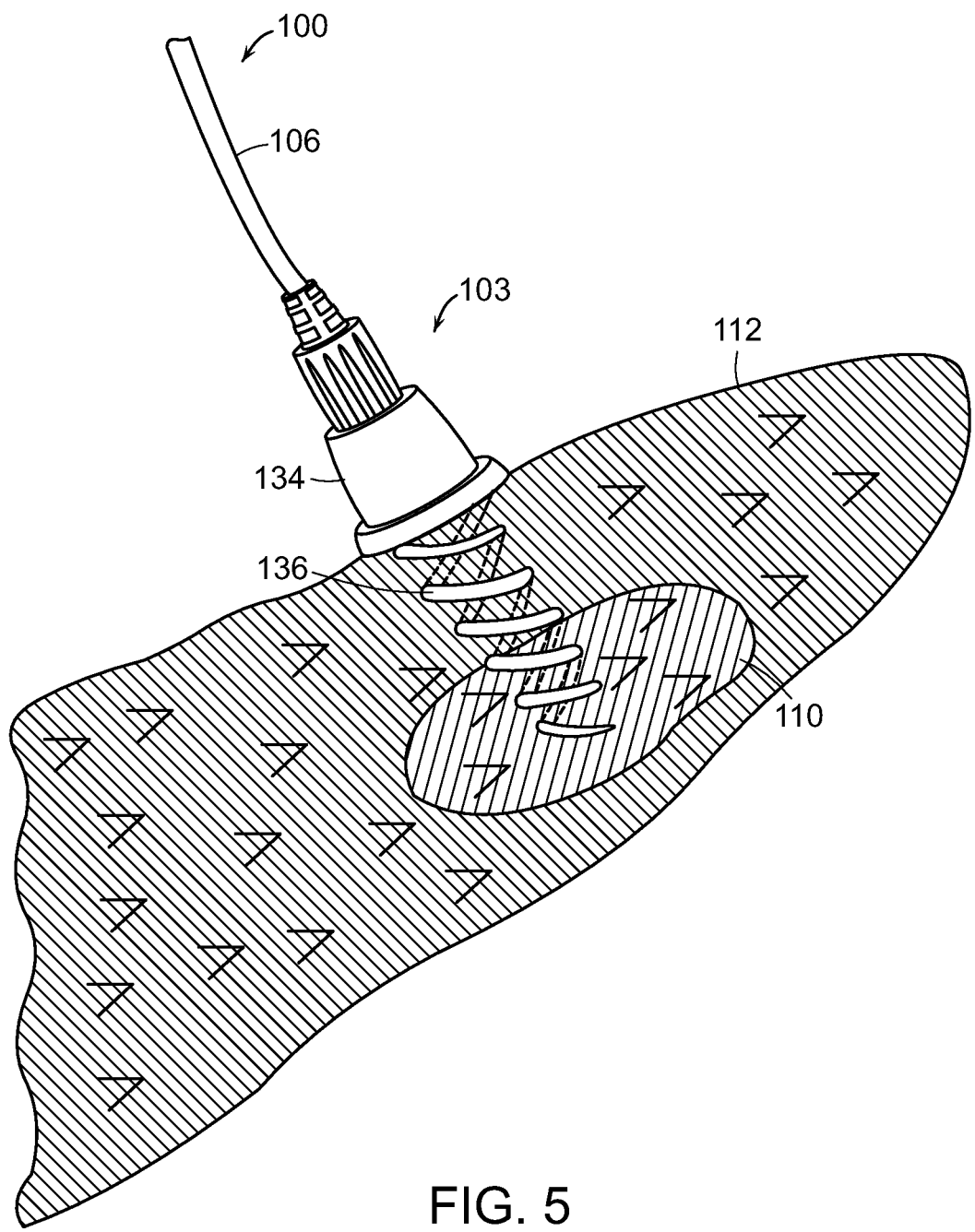
FIG. 5 is a cross-sectional view of one embodiment of an electrical ablation device shown in use in treatment of abnormal tissues or growths, such as cancers or tumors, formed in solid organs.

FIG. 5 is a cross-sectional view of one embodiment of the electrical ablation device 100 shown in use in treatment of abnormal tissues or growths, such as cancers or tumors, formed in solid organs. In the embodiment illustrated in FIG. 5, an electrode 136 located at the distal end 103 of the electrical ablation device 100 is embedded into the tumor 110 formed in the liver 112. The distal end 103 of the electrical ablation device 100 comprises a connector 134 adapted to couple to the cable 106. The electrode 136 is adapted to embed into the liver 112 and the tumor 110. In the illustrated embodiment, the electrode 136 has a helical body (e.g., corkscrew) to penetrate and attach the electrode 136 into the liver 112 and the tumor 110. The electrode 136 comprises at least one electrically conductive portion formed of or coated with an electrically conductive material such as medical grade stainless steel, for example. In one embodiment, the electrode 136 may be configured as an anode (+) coupled to a positive terminal of the energy source 119. A second electrode may be configured as a cathode (−) coupled to a negative terminal of the energy source 119 to form a conductive return path or surface and may be located in the stomach 108 or elsewhere. It will be appreciated that the electrode 136 may be configured either as the anode (+) or the cathode (−) and the polarity of the electrode 136 may be reversed by reversing the output of the energy source 119. In one embodiment, the second electrode may be an electrically conductive balloon (not shown) located in the stomach 108 or other internal body lumen. The first and second electrodes may be inserted inside the patient's body using laparoscopic or endoscopic minimally invasive surgical techniques.

Referring to FIGS. 1-5, in one embodiment, the connector 114 and either one of the electrodes 104, 134 may be introduced into a hollow body lumen via a flexible endoscope using translumenal endoscopic access techniques. For convenience and brevity, the following process is described with reference only to the electrode 104 shown in FIGS. 1 and 4; however, those skilled in the art will appreciate that these techniques may be used in regards to the electrode 136 shown in FIG. 5 as well. A flexible endoscope is introduced into a natural body orifice such as the mouth, anus, or vagina. For example, the flexible endoscope may be introduced into the stomach 108 trans-orally. The cable 106 and the electrode 104 may be introduced into the stomach 108 through the working channel of the endoscope. An opening is formed through the wall 118 of the stomach 108 using translumenal access techniques, described in more detail below. The cable 106 and the electrode 104 are fed through the opening in the wall 118. The electrode 104 is inserted into the liver 112 and the tumor 110 and is secured or attached therein by the ridges 105 formed on the electrode 104. If the electrode 136 were being used, the helical body of the electrode 136 serves to penetrate and retain the electrode 136 in the liver 112 and the tumor 110. As shown in FIG. 2, the connector 114 is then attached to the wall 118 of the stomach 108 with sutures or tags inserted through the one or more openings 124 formed in the flanges 122a, b. Once the connector 114 is attached to the wall 118 of the stomach 108, the plug 115 and cable 117 may be inserted trans-orally through a working channel of the endoscope. The plug 115 is electrically coupled to the connector 114 inside the stomach 108. The plug 115 includes corresponding female receptors to receive the one or more terminals 128a, 128b and form an electrical connection. The first and second recesses 126a (FIG. 3), 126b (126b not shown) formed in the body 120 receive corresponding tabs formed on the mating female plug 115 portion to removably attach the plug 115 to the connector 114. The proximal end of the cable 117 is connected to the energy source 119 outside the patient's body. The electrical ablation therapy is then applied to the tumor 110.

Once the electrical ablation device 100 is positioned and the electrical connections are completed, the tumor 110 may be treated with electrical ablation energy supplied by the energy source 119. The electrical ablation energy may be delivered in many forms, as described in more detail below. Following the electrical ablation therapy, the plug 115 and the cable 117 are removed from the patient after disconnecting the plug 115 from the connector 114. If subsequent electrical ablation therapy is necessary to completely ablate the tumor 110, the plug 115 and the cable 117 are reinserted into the patient, the plug 115 is connected to the connector 114 and electrical ablation therapy is reinitiated. The tumor 110 may be monitored over time (e.g., days, weeks, or months) to observe shrinkage. The electrical ablation therapy may be repeated until the tumor 110 disappears. The electrical ablation device 100 remains inside the patient until the treatment of the tumor 110 is completed.

The electrical ablation device 100 is driven with electrical ablation energy supplied by the energy source 119 shown in FIG. 1. The input to the energy source 119 is connected to a commercial power supply by way of a plug (not shown). The output of the energy source 119 is coupled to the electrodes (e.g., electrode 104 or electrode 136) and energized with electrical ablation energy suitable to ablate abnormal (e.g., cancerous) tissues and destroy the tumor 110, for example. The energy source 119 may be configured to produce electrical ablation energy in various forms, as described in more detail below.

In one embodiment, the energy source 119 may be configured to produce pulsed or cyclical electrical ablation signals to electrically ablate abnormal tissue with the electrical ablation device 100. In one embodiment, a timing circuit may be used to interrupt the output of the energy source 119 and generate a pulsed output signal. The timing circuit may comprise one or more suitable switching elements to produce the pulsed output signal. For example, the energy source 119 may produce a series of n pulses (where n is any integer) suitable to treat the tumor 110 when the pulsed energy is applied to the electrodes (e.g., electrode 104 or electrode 136). The pulses may have a fixed or variable pulse width and may be delivered at any suitable frequency.

In one embodiment, the energy source 119 may be configured to produce electrical output waveforms at predetermined frequencies, amplitudes, polarities, and/or pulse widths to electrically ablate abnormal tissue with the electrical ablation device 100. When the electrical output waveforms are applied to the electrodes (e.g., electrode 104 or electrode 136), the resulting electric potentials cause currents to flow through the distal end of the electrodes to destroy abnormal tissue such as the tumor 110.

In one embodiment, the energy source 119 may be configured to produce radio frequency (RF) waveforms at predetermined frequencies, amplitudes, polarities, and pulse widths to electrically ablate abnormal tissue with the electrical ablation device 100. The energy source 119 may comprise a commercially available conventional, bipolar/monopolar electrosurgical RF generator such as Model Number ICC 350, available from Erbe, GmbH.

In one embodiment, the energy source 119 may be configured to produce irreversible electroporation (IRE) energy in the form of bipolar/monopolar pulsed DC output signals to electrically ablate abnormal tissue with the electrical ablation device 100. The energy source 119 may comprise a commercially available conventional, bipolar/monopolar Pulsed DC generator such as Model Number ECM 830, available from BTX Molecular Delivery Systems Boston, Mass. In bipolar mode a first electrode (e.g., electrode 104 or electrode 136)

may be electrically coupled to a first polarity and a second electrode may be electrically coupled to a second (e.g., opposite) polarity. Bipolar/monopolar pulsed DC output signals (e.g., DC pulses) may be produced at a variety of frequencies, amplitudes, pulse widths, and polarities. For example, the energy source 119 may be configured to produce DC pulses at frequencies in the range of about 1 Hz to about 1000 Hz, amplitudes in the range of about ±100 to about ±3000 VDC, and pulse widths (e.g., pulse durations) in the range of about 1 µs to about 100 ms to electrically ablate the tumor 110. The polarity of the energy delivered to the electrodes (e.g., electrode 104 or electrode 136) may be reversed during the electrical ablation therapy. For example, the polarity of the DC pulses initially delivered at amplitudes in the range of about +100 to about +3000 VDC may be reversed to amplitudes of about −100 to about −3000 VDC. Preferably, the tumor 110 may be electrically ablated with DC pulses at frequencies of about 10 Hz to about 100 Hz, amplitudes in the range of about +700 to about +1500 VDC, and pulse widths of about 10 µs to about 50 µs. The IRE energy also may be used for the treatment of BPH and restricted gastric tissue.

In one embodiment, the energy source 119 may energize the electrode 104 through a wired or a wireless connection. In a wired connection, the energy source 119 is coupled to the electrode by way of one or more electrically conductive wires through the cable 106. As previously discussed, the cable 106 may connected to the connector 114, which may be inserted transmurally through a hollow body lumen, such as the wall 118 of the stomach 108, or percutaneously through the abdominal wall 109. In a wireless connection, the energy source 119 may be coupled to the electrode 104 by way of one or more antennas, thus eliminating the need to perforate the hollow body lumen or the patient's skin. In a wireless embodiment, the cable 106 may be replaced by an antenna 904 as shown in FIG. 19, for example. The antenna 904 is coupled to the electrode by an electrically conductive wire.

Figure 6:
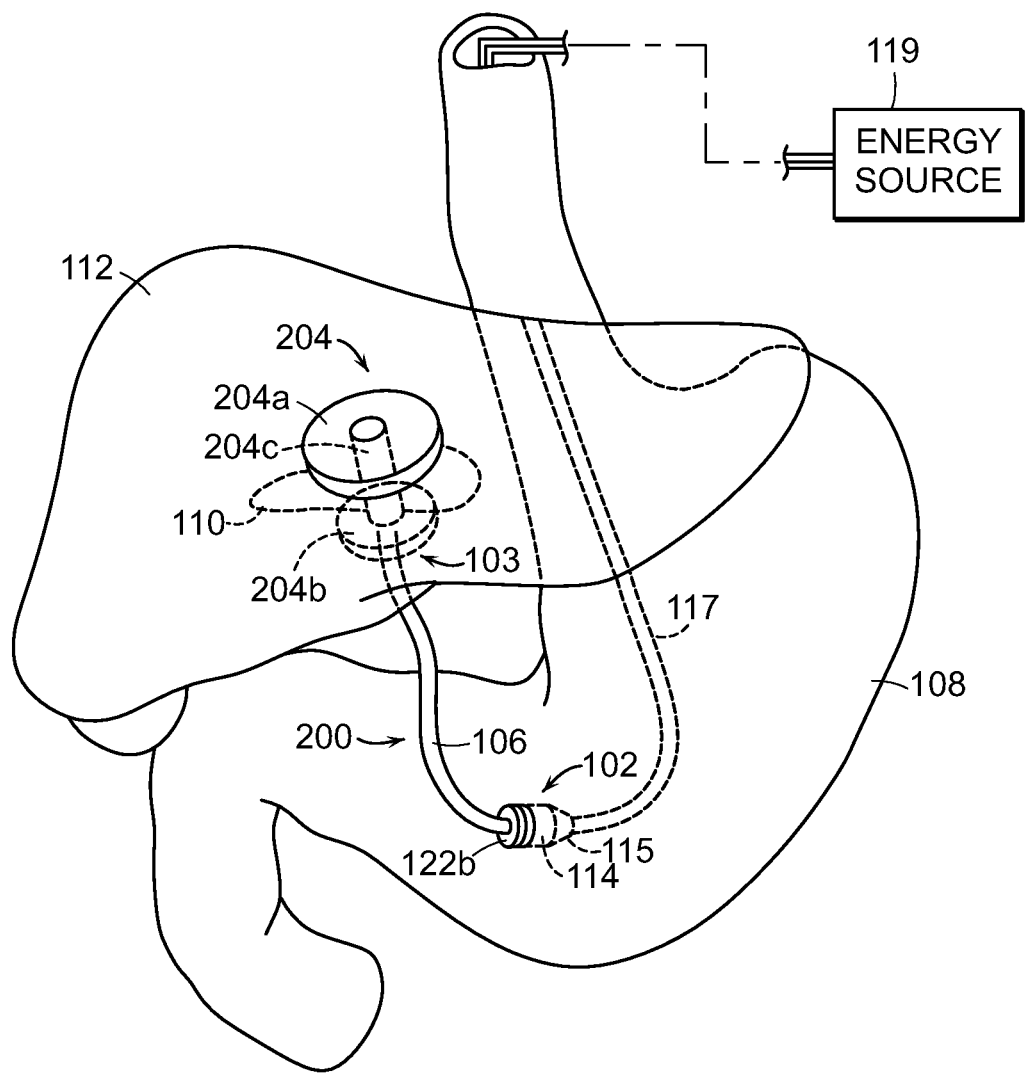
FIG. 6 illustrates one embodiment of an electrical ablation device shown in use.

FIG. 6 illustrates one embodiment of an electrical ablation device 200 shown in use. In one embodiment, the electrical ablation device 200 may be used in treatment of abnormal tissues or growths, such as cancers or tumors, formed in or on solid organs, BPH, and restricted gastric tissue using IRE energy. In other embodiments, electrical ablation treatment may be applied using other forms of electrical energy, such as those described herein. In one embodiment, the electrical ablation device 200 comprises the connector 114 at the proximal end 102 and an electrode assembly 204 at the distal end 103. As previously discussed, the connector 114 is configured for attachment through the wall 118 of a hollow body lumen such as the stomach 108 to couple the electrical ablation device 200 to the energy source 119. The electrode assembly 204 is configured to attach to solid organ such as the liver 112 and electrically ablate abnormal tissues or growths such as the tumor 110 formed in the liver 112. As illustrated in FIG. 6, the connector 114 is attached to the wall 118 of the stomach 108 and the electrode assembly 204 is positioned on exterior surfaces of the liver 112 proximal to the tumor 110. The tumor 110 may be electrically ablated by the electrical ablation device 200 with electrical ablation energy supplied by the energy source 119.

The proximal end 102 of the electrical ablation device 200 is attached to the stomach 108 via the connector 114. As previously discussed, the connector 114 is attached to the wall 118 of the stomach 108 with sutures or tags inserted through the one or more openings 124 formed in the flanges 122a, b of the connector 114 as shown in FIG. 2. The connector 114 receives the corresponding mating female plug 115 inside the stomach 108 to electrically couple the energy source 119 to the electrical ablation device 200.

The distal end 103 of the electrical ablation device 200 is attached to the liver 112 via the electrode assembly 204. In one embodiment, the electrode assembly 204 comprises first and second plate electrodes 204a, 204b configured as electrodes and a center post 204c extending therebetween. The first and second plate electrodes 204a, b each comprise openings to receive the center post 204c. The center post 204c is inserted through the tumor 110 and through the openings formed in the first and second plate electrodes 204a, b. The first and second plate electrodes 204a, b are positioned opposite each other on outer surfaces of the liver 112. The first and second plate electrodes 204a, b are slidably movable along an outer surface of the center post 204c. Thus, the distance D (shown in FIGS. 7A and 7C) between the first and second plate electrodes 204a, b may be adjusted according to the size of the liver 112. In the illustrated embodiment, the first plate electrode 204a is located above the tumor 110 and the second plate electrode 204b is located below the tumor 110. Once positioned, the first and second plate electrodes 204a, b may be adjusted to slightly compress the liver 112. The first and second plate electrodes 204a, b each comprises at least one electrically conductive portion that is formed of or coated with an electrically conductive material such as medical grade stainless steel, for example, and are electrically coupled to respective first and second electrically conductive wires of the cable 106 to deliver electrical ablation energy to the tumor 110 from the energy source 119. The center post 204c is formed of an electrically insulative material such as medical grade polyester, for example, to electrically isolate the center post 204c from the first and second plate electrodes 204a, b. In one embodiment the first plate electrode 204a may be configured as the anode (+) electrode coupled to the positive terminal of the energy source 119 and the second plate electrode 204b may be configured as the cathode (−) electrode coupled to the negative terminal of the energy source 119. It will be appreciated that the polarity of the first and second plate electrodes 204a, b may be reversed such that the first plate electrode 204a is configured as the cathode (−) electrode and the second plate electrode 204b is configured as the anode (+) electrode by reversing the output polarity of the energy source 119.

Figure 20:
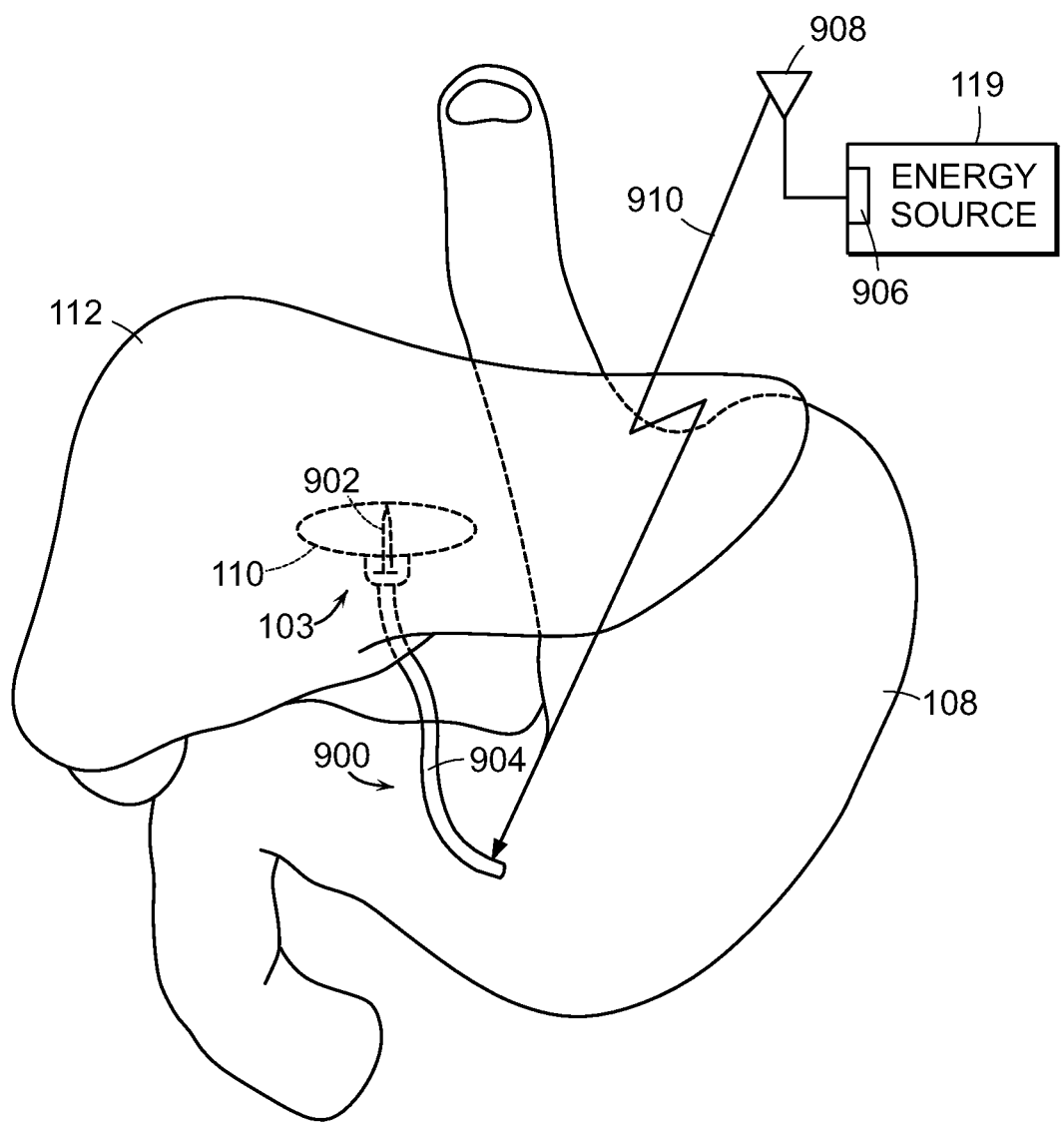
FIG. 20 illustrates one embodiment of a wireless electrical ablation device shown in use.

In one embodiment, electrical ablation device 200 including the first and second plate electrodes 204a, b may be introduced to the treatment site (e.g., the tumor 110) endoscopically, laparoscopically, or through various translumenal access techniques. As previously discussed, a flexible endoscope may be introduced into the stomach 108 trans-orally and the cable 106 may be fed through the access or working channel of the endoscope. The cable 106 and the electrode 104 are initially placed in the stomach 108. The wall 118 of the stomach 108 is perforated using translumenal access techniques. The cable 106 and the electrode assembly 204 are advanced through the trans-mural opening and the electrode assembly 204 is attached to the liver 112. The plug 115 and the cable 117 are then inserted trans-orally through the working channel of the endoscope. The plug 115 at the distal end of the cable 117 is electrically coupled to the connector 114 inside the stomach 108. The proximal end of the cable 117 is connected to the energy source 119 outside the patient's body. The tumor 110 is then treated with electrical ablation energy supplied by the energy source 119. After the electrical ablation therapy is completed, the plug 115 may be removed from the connector 114 and the plug 115 and the cable 117 removed from inside the patient. The plug 115 and the cable 117 may be reinserted into the patient for subsequent electrical ablation therapy. The tumor 110 may be monitored over time (e.g., days, weeks, or months) to observe shrinkage. The electrical ablation therapy may be repeated until the tumor 110 disappears. The electrical ablation device 200 remains inside the patient until the tumor 110 is completely ablated. It will be appreciated that the electrode assembly 204 may be repositioned to treat tumors that are larger than the surface area of the first and second plate electrodes 204a, b. In various other embodiments, the first and second plate electrodes 204a, b of the electrical ablation device 200 may be coupled to the energy source 119 percutaneously through the abdominal wall 109 (FIG. 19) or wirelessly by replacing the cable 106 with the antenna 904 (FIG. 20). The antenna 904 is coupled to the first plate electrode 204a by a first electrically conductive wire and the antenna 904 is coupled to the second plate electrode 204b by a second electrically conductive wire.

Figure 7A:
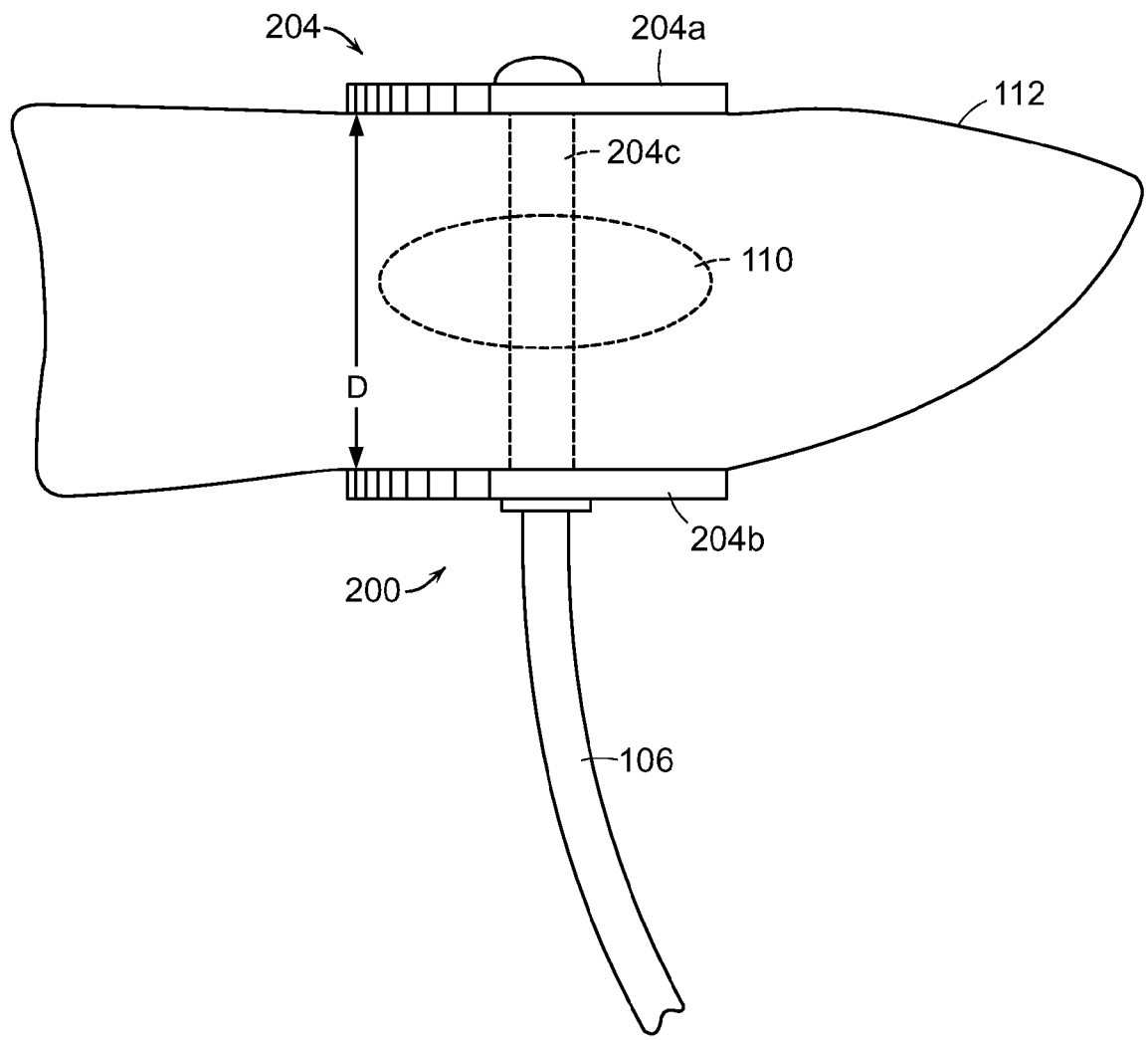
FIG. 7A is a side view of one embodiment of the electrical ablation device in FIG. 6 attached to the liver.
Figure 7B:
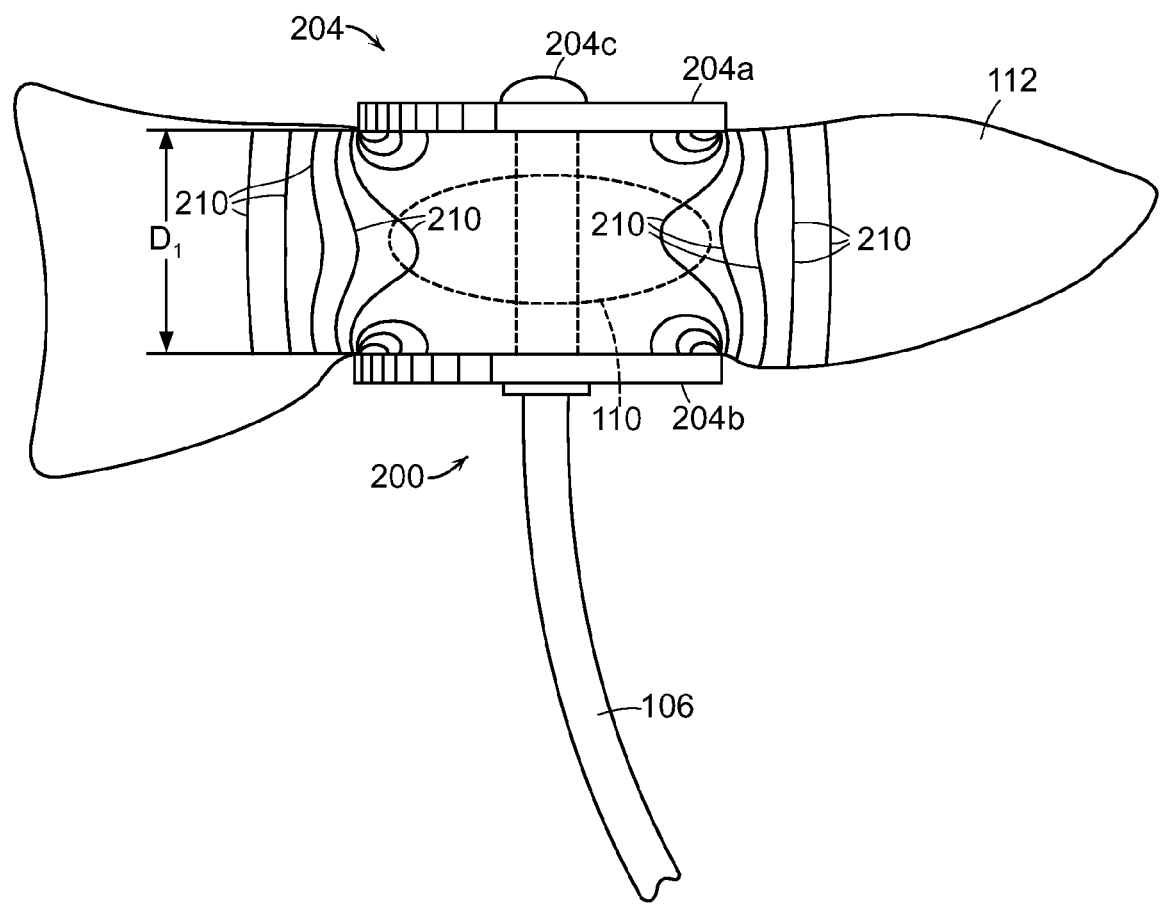
FIG. 7B is a side view of the electrical ablation device in FIG. 6 with first and second plate electrodes slidably moved toward each other along the outer surface of a center post to compress the liver and concentrate the energy delivered to the tumor.

FIGS. 7A and 7B are side views of one embodiment of the electrical ablation device 200 shown in use in treatment of a tumor formed in a solid organ using IRE energy. As shown in FIG. 7A, the electrical ablation device 200 is attached to the liver 112. The first and second plate electrodes 204a, b are placed above and below the tumor 110 on the outer surface of the liver 112. In FIG. 7B, the first and second plate electrodes 204a, b have been slidably moved toward each other along the outer surface of the center post 204c to compress the liver 112 to a distance $D_1$, which is less than the distance D shown in FIG. 7A. Compression of the liver 112 helps to concentrate the energy delivered to the tumor 110 as well as reduce the voltage required to ablate the tumor 110. Furthermore a more homogeneous electric field can be applied with using the parallel plates configuration of the first and second plate electrodes 204a, b. The first and second plate electrodes 204a, b are electrically coupled to the energy source 119 (FIG. 6) via the cable 106. The output of the energy source 119 is set to create a voltage difference between the first and second plate electrodes 204a, b that is high enough to produce an electric field, represented by iso-lines 210, sufficient to electrically ablate the tumor 110. The potential energy level of the electric field may be in the order of about 1e5 volts/meter. The potential energy level is sufficient to destroy the tumor 110 and the tissue surrounding the tumor 110.

Figure 7C:
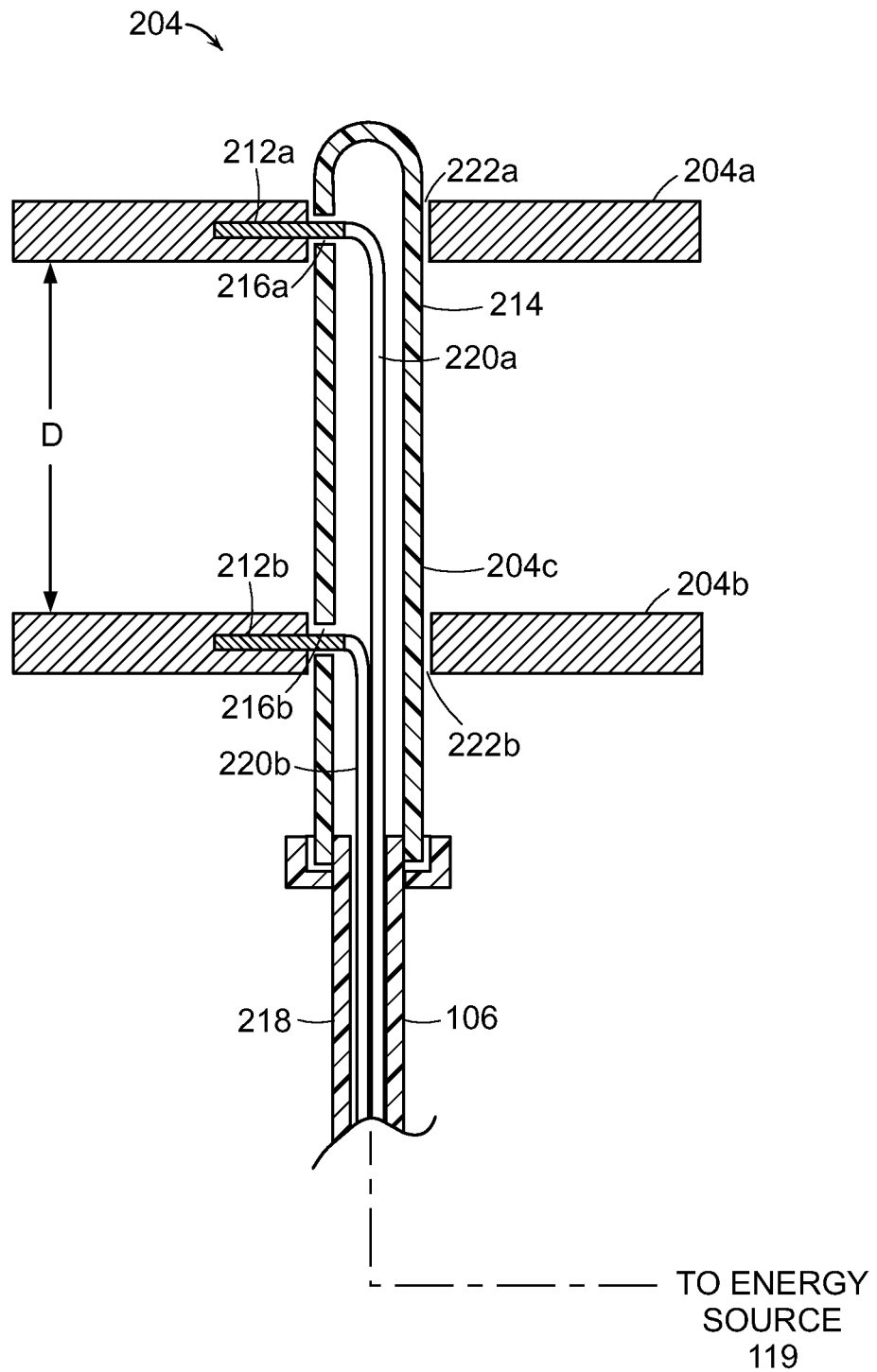
FIG. 7C is a cross-sectional view of one embodiment of the electrical ablation device in FIGS. 7A and 7B.

FIG. 7C is a cross-sectional view of one embodiment of the electrical ablation device 200. The first and second plate electrodes 204a, b are separated by a distance D, which is adjustable by slidably moving the first and second plate electrodes 204a, b along an outer surface 214 of the center post 204c. First and second conductors 212a, 212b are electrically connected to the respective first and second plate electrodes 204a, b. The first and second conductors 212a, b are provided through respective openings 216a, 216b formed through the center post 204c. The first and second conductors 212a, b are contained in respective insulative sheathes 220a, b and are housed within an electrically insulative outer sheath 218 of the cable 106. In the illustrated embodiment, the first and second conductors 212a, b are coupled to the respective positive (+) and negative (−) terminals of the energy source 119 (FIG. 6) through the connector 114 (FIG. 6), for example. In other embodiments, the polarity of the first and second conductors 212a, b may be reversed. The first and second plate electrodes 204a, b may be locked into position against the center post 204c once adequate compression has been applied to the liver 112 as shown in FIG. 7B. In one embodiment, the first and second plate electrodes 204a, b are maintained at a desired distance D from each other by frictionally engaging the outer surface 214 of the center post 204c with the inner surfaces defined by the openings 222a, 222b. In other embodiments, various features may be provided on the outer surface 214 of the center post 204c and the inner surface defined by the openings 222a, 222b in the respective first and second plate electrodes 204a, b to lock the first and second plate electrodes 204a, b at a desired distance D from each other. These features may include corresponding male and female threaded surfaces, ratcheting surfaces, and grooves with detents, for example.

With reference to FIGS. 6 and 7A-C, the tumor 110 may be electrically ablated by applying IRE energy to the first and second plate electrodes 204a, b of the electrode assembly 204. As previously discussed, the energy source 119 DC pulses at frequencies in the range of about 1 Hz to about 1000 Hz, amplitudes in the range of about ±100 to about ±3000 VDC, and pulse widths (e.g., pulse durations) in the range of about 1 µs to about 100 ms to the first and second plate electrodes 204a, b of the electrode assembly 204. The polarity of the energy delivered to the electrodes (e.g., electrode 104 or electrode 136) may be reversed during the electrical ablation therapy. For example, the polarity of the DC pulses initially delivered at amplitudes in the range of about +100 to about +3000 VDC may be reversed to amplitudes of about −100 to about −3000 VDC. Preferably, the tumor 110 may be electrically ablated with DC pulses at frequencies of about 10 Hz to about 100 Hz, amplitudes in the range of about +700 to about +1500 VDC, and pulse widths of about 10 µs to about 50 µs.

FIGS. 8A-D are side views of one embodiment of an electrical ablation device 300 shown in various stages of deployment. In one embodiment, the electrical ablation device 300 may be used in treatment of abnormal tissues or growths, such as cancers or tumors, formed in or on solid organs, BPH, and restricted gastric tissue using IRE energy. The electrical ablation device 300 may be used to electrically ablate abnormal tissues or growths, such as cancers or tumors, formed in solid organs using IRE energy. In other embodiments, electrical ablation treatment may be applied using other forms of electrical energy, such as those described herein.

Figure 8A:
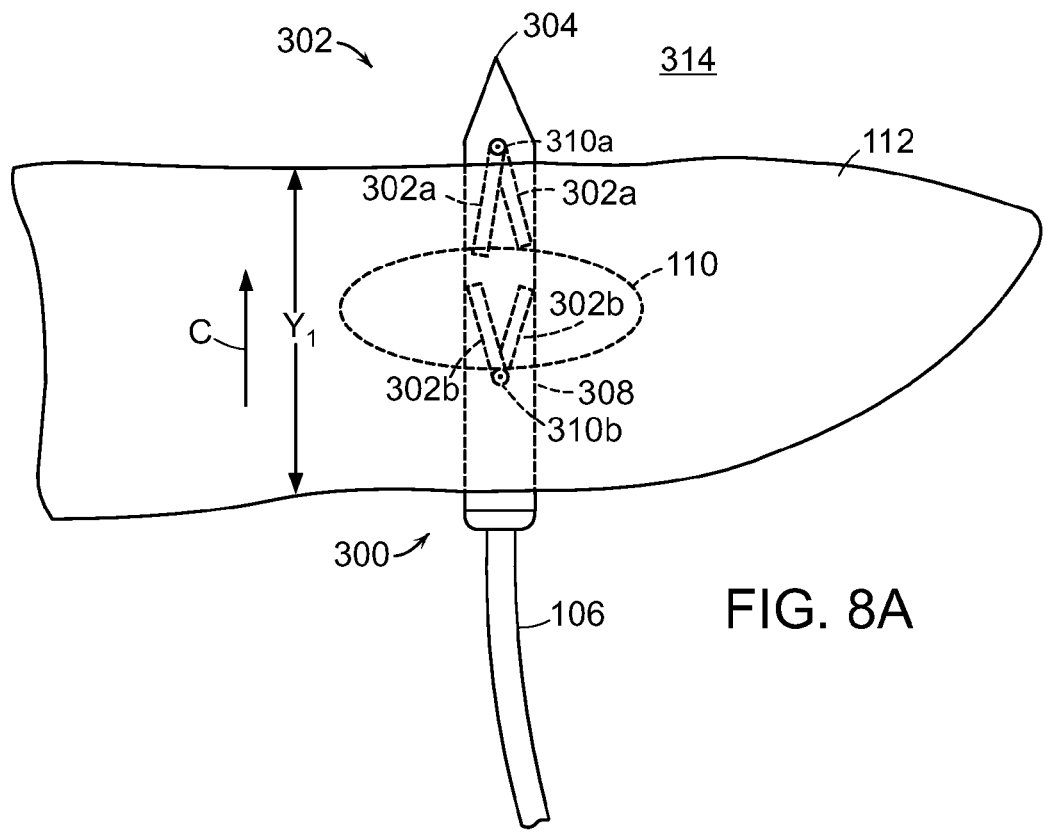
FIG. 8A illustrates one embodiment of an electrical ablation device being deployed through a tumor in the liver.

FIG. 8A illustrates one embodiment of the electrical ablation device 300 being deployed through the tumor 110 and the liver 112. In the illustrated embodiment, the electrical ablation device 300 comprises an electrode assembly 302 that is attachable to a solid organ such as the liver 112. In one embodiment, the electrode assembly 302 comprises a sharp distal end 304 suitable for penetrating the liver 112 and the tumor 110. The electrode assembly 302 comprises first and second arm electrodes 302a, 302b configured as first and second electrodes. The first and second arm electrodes 302a, b are initially folded and contained within a hollow body 308 of the electrode assembly 302 to enable the electrode to pierce and penetrate the liver 112 and the tumor 110 with the sharp distal end 304. The first and second arm electrodes 302a, b each comprises at least one electrically conductive portion that is formed of or coated with an electrically conductive material such as medical grade stainless steel, for example, and are coupled to the energy source 119 (previously described with reference to FIGS. 1-5) through one or more electrically conductive wires 220a, b that form the cable 106 as shown in FIG. 7C. The hollow body 308 is formed of an electrically insulative material such as medical grade polyester, for example, to electrically isolate the hollow body 308 from the first and second arm electrodes 302a, b. In one embodiment the first arm electrode 302a may be configured as the anode (+) electrode coupled to the positive terminal of the energy source 119 and the second arm electrode 302b may be configured as the cathode (−) electrode coupled to the negative terminal of the energy source 119. It will be appreciated that the polarity of the first and second arm electrodes 302a, b may be reversed such that the first arm electrode 302a is configured as the cathode (−) electrode and the second arm electrode 302b is configured as the anode (+) electrode by reversing the output polarity of the energy source 119.

As previously discussed, the cable 106 is attached to the connector 114 through the wall 118 of the stomach 108 using techniques previously described with reference to FIGS. 1-3 and 6, for example. The first and second arm electrodes 302a, b are pivotably movable about respective pivot points 310a, 310b. In various other embodiments, the first and second arm electrodes 302a, b of the electrical ablation device 300 may be coupled to the energy source 119 percutaneously through the abdominal wall 109 (FIG. 19) or wirelessly by replacing the cable 106 with the antenna 904 (FIG. 20). The antenna 904 is coupled to the first arm electrode 302a by a first electrically conductive wire and the antenna 904 is coupled to the second arm electrode 302b by a second electrically conductive wire.

Figure 8B:
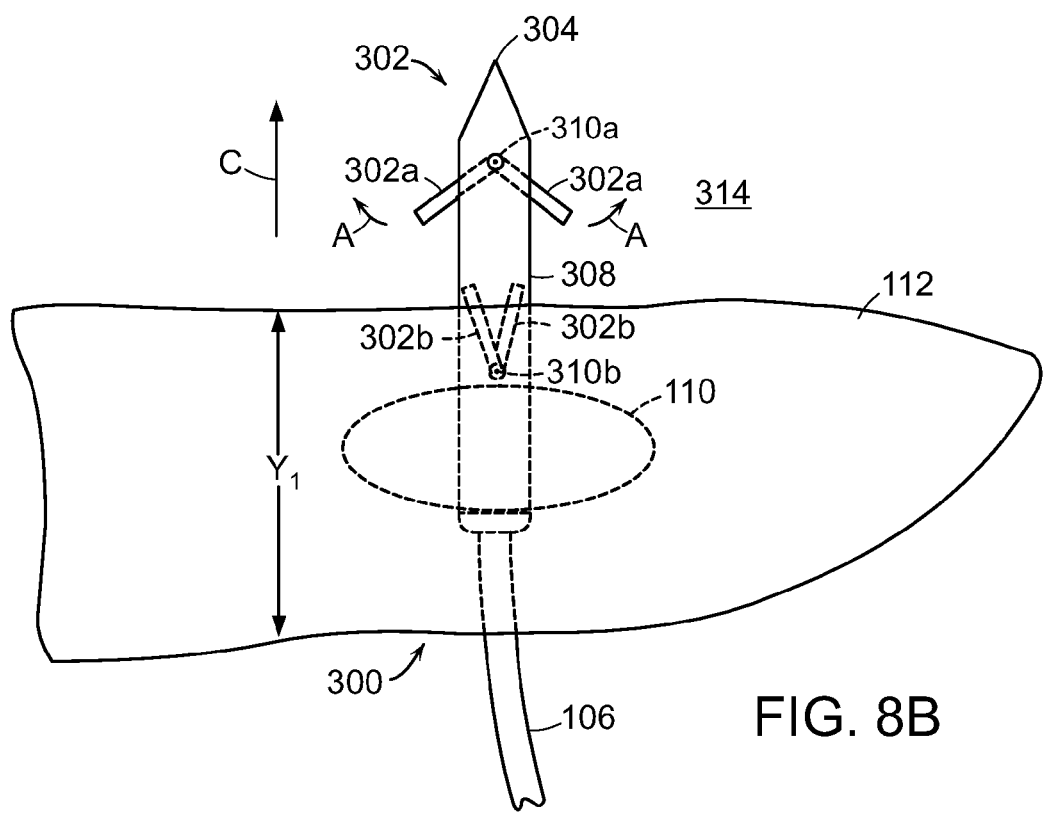
FIG. 8B illustrates one embodiment of the electrical ablation device in FIG. 8A with a first arm electrode deployed.
Figure 8C:
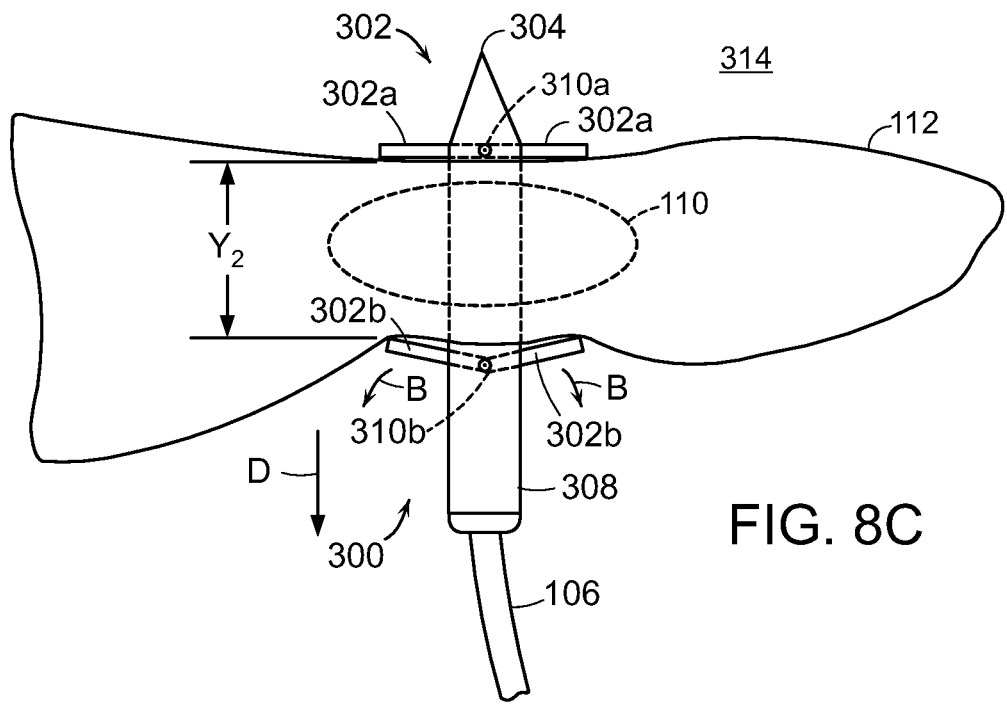
FIG. 8C illustrates one embodiment of the electrical ablation device in FIG. 8A with first and second arm electrodes deployed.
Figure 9:
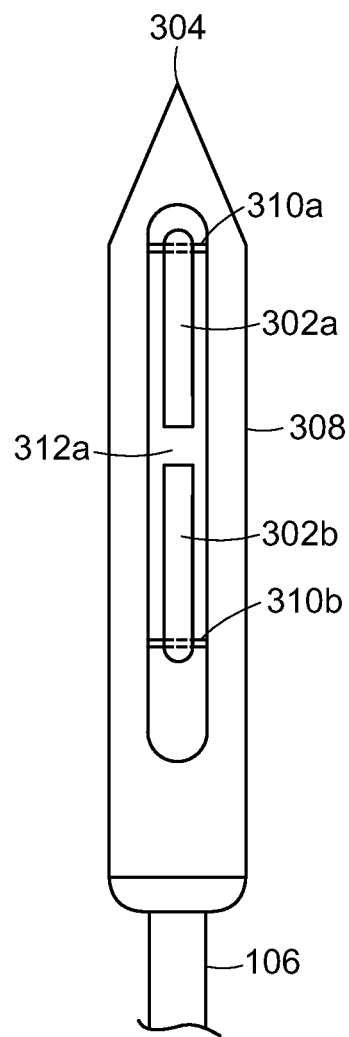
FIG. 9 is a side view of one embodiment of the electrical ablation device in FIG. 8A.
Figure 10:
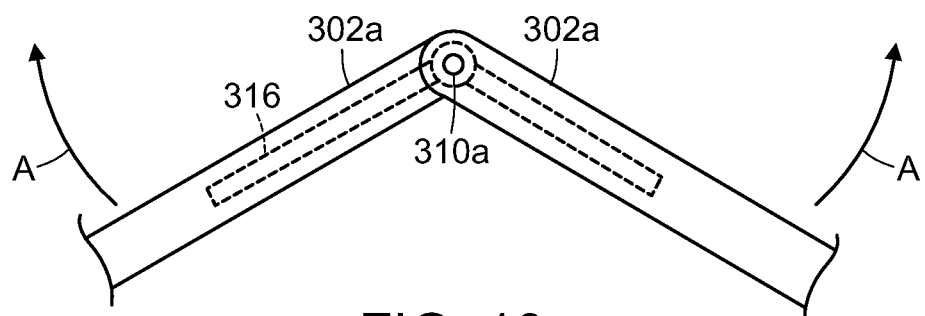
FIG. 10 illustrates a spring-loaded arm portion of one embodiment of the electrical ablation device in FIG. 9.

FIG. 9 is a side view of one embodiment of the electrical ablation device 300. FIG. 10 illustrates a spring-loaded arm portion of the embodiment of the electrical ablation device 300 shown in FIG. 9. As shown in FIGS. 8B, 8C, 9, and 10, the first and second arm electrodes 302a, b are pivotally movable outwardly in the directions shown by arrows A and B through respective longitudinal slots 312a, 312b formed in the hollow body 308 of the electrode assembly 302. In one embodiment, the first and second arm electrodes 302a, b are spring loaded and may be actuated by internal springs or other actuation mechanisms. As shown in FIG. 10 the first arm electrode 302a comprises a spring 316 to open the first arm electrode 302a outwardly in direction A. Although not shown, the second arm electrode 302b also comprises a spring 316 to open the second arm electrode 302b outwardly in direction B.

Figure 8D:
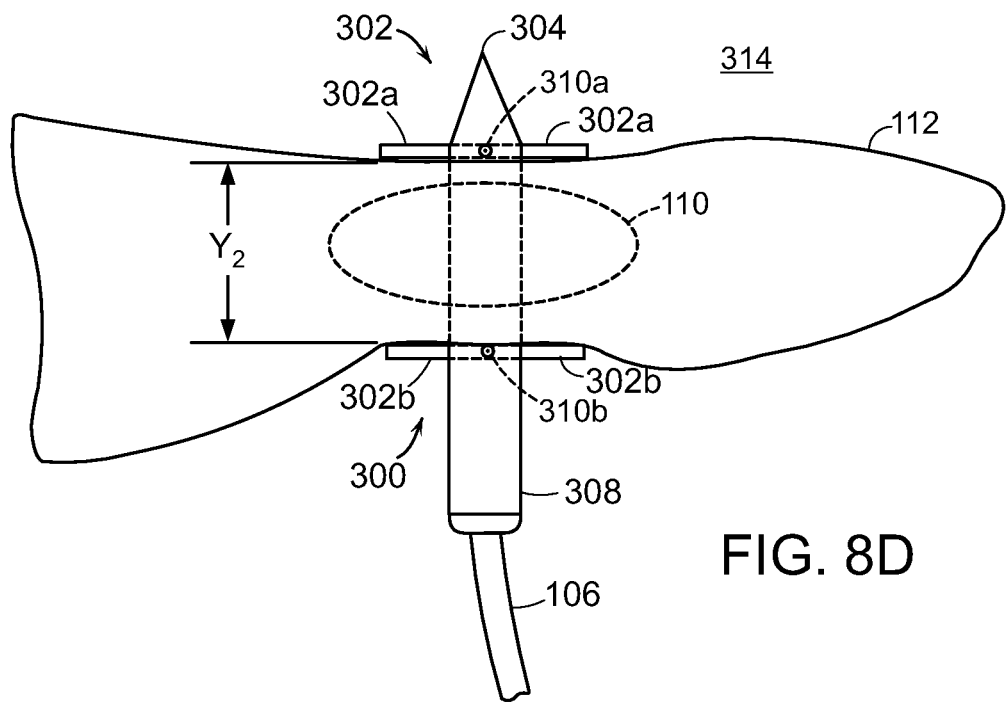
FIG. 8D illustrates the liver slightly compressed by the first and second arm electrodes of the electrical ablation device in FIG. 8A.

Referring to FIGS. 8A-D, the illustrated embodiment of the electrical ablation device 300 is shown in use in treatment of the tumor 110 formed in the liver 112 using electrical energy. As shown in FIG. 8A, the first and second arm electrodes 302a, b are folded and spring loaded inside the hollow body 308 of the electrode assembly 302. The distal end 304 of the electrode assembly 302 is inserted in direction C into one side of the liver 112, through the tumor 110, and out the other side of the liver 112. As shown in FIG. 8B, the distal end 304 of the electrode assembly 302 is pushed in direction C through the other side of the liver 112 until the first arm electrode 302a is exposed in the hollow body lumen 314 surrounding the liver 112 enabling the first arm electrode 302a to spring open in direction A under the force of the spring 316 (FIG. 10). Once the first arm electrode 302a is deployed, the electrode assembly 302 is retracted by pulling in direction D until the second arm electrode 302b is exposed in the hollow body lumen 314 surrounding the liver 112 and enabling the second arm electrode 302b to open in direction B, as shown in FIG. 8C. As shown in FIG. 8D the liver 112 may be slightly compressed such that $y_2 < y_1$, where $y_1$ is the pre-compressed thickness of the liver 112 and $y_2$ is the compressed thickness of the liver 112.

As shown in FIG. 8D, the tumor 110 may be electrically ablated by applying IRE energy to the electrode assembly 302 when the first and second arm electrodes 302a, b are deployed. As previously discussed, the energy source 119 (previously described with reference to FIGS. 1-5) supplies DC pulses at frequencies in the range of about 1 Hz to about 1000 Hz, amplitudes in the range of about ±100 to about ±3000 VDC, and pulse widths (e.g., pulse durations) in the range of about 1 μs to about 100 ms to the electrode assembly 302. The polarity of the energy delivered to the first and second arm electrodes 302a, b electrodes may be reversed during the electrical ablation therapy. For example, the polarity of the DC pulses initially delivered at amplitudes in the range of about +100 to about +3000 VDC may be reversed to amplitudes of about −100 to about −3000 VDC. Preferably, the tumor 110 may be electrically ablated with DC pulses at frequencies of about 10 Hz to about 100 Hz, amplitudes in the range of about +700 to about +1500 VDC, and pulse widths of about 10 μs to about 50 μs.

Figure 11B:
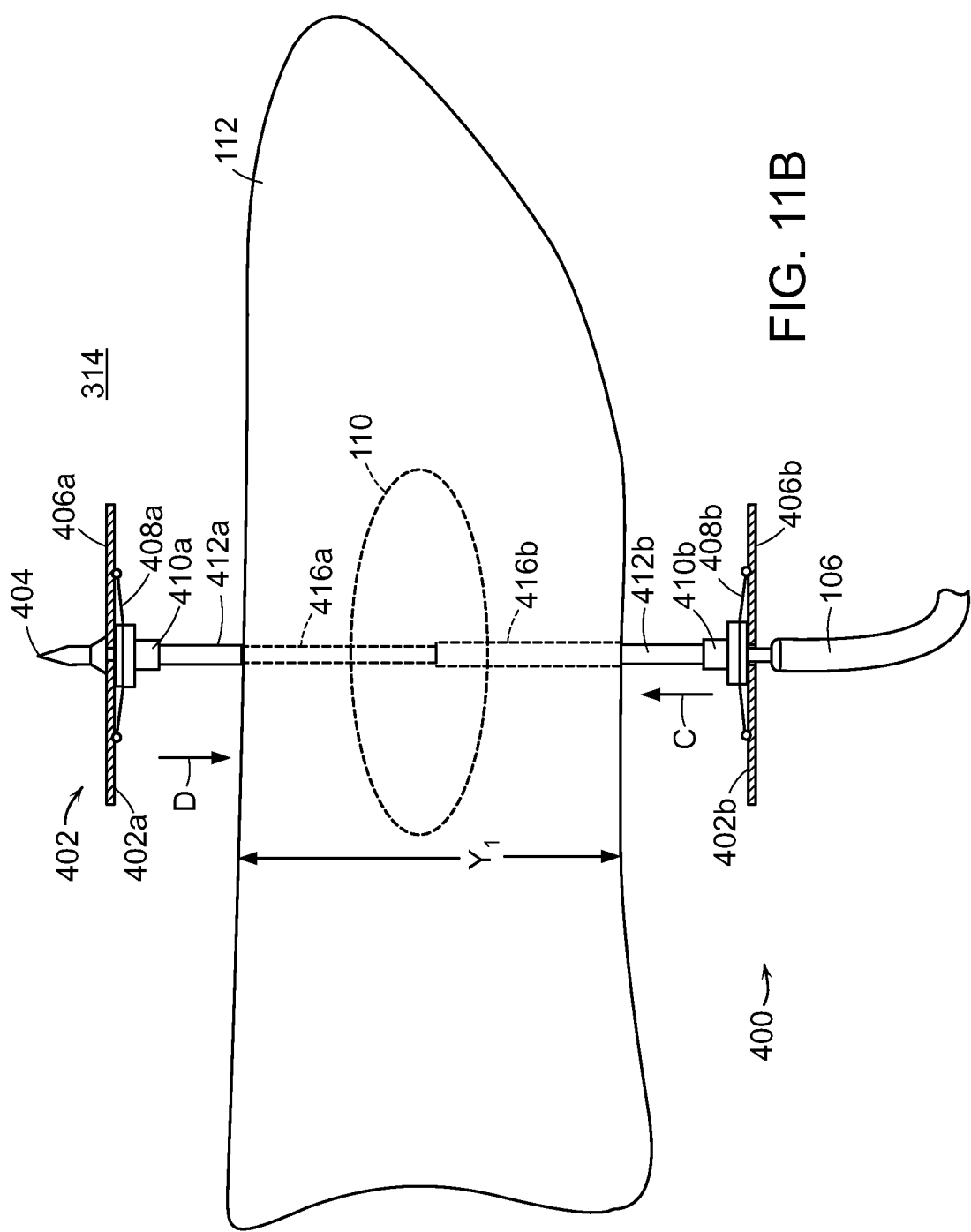
FIG. 11B illustrates first and second electrodes of one embodiment of the electrical ablation device in FIG. 11A slidably opened.

FIGS. 11A-C are side views of one embodiment of an electrical ablation device 400 shown in various stages of deployment. In one embodiment, the electrical ablation device 400 may be used in treatment of abnormal tissues or growths, such as cancers or tumors, formed in or on solid organs, BPH, and restricted gastric tissue using IRE energy. In other embodiments, electrical ablation treatment may be applied using other forms of electrical energy, such as those described herein. FIG. 11A illustrates one embodiment of the electrical ablation device 400 being deployed through the tumor 110 and the liver 112. In the illustrated embodiment, the electrical ablation device 400 comprises an electrode assembly 402 that is attachable to a solid organ such as the liver 112. In one embodiment, the electrode assembly 402 comprises a sharp distal end 404 adapted to pierce and penetrate the liver 112 and the tumor 110. The sharp distal end 404 can be inserted into one side of the liver 112, through the tumor 110, and out the opposite side of the liver 112. In one embodiment, the electrode assembly 402 comprises a first canopy electrode 402a and a second canopy electrode 402b. The first and second canopy electrodes 402a, b each comprises at least one electrically conductive portion that is formed of or coated with an electrically conductive material such as medical grade stainless steel, for example, and are coupled to the energy source 119 (previously described with reference to FIGS. 1-5) through one or more electrically conductive wires 220a, b that form the cable 106 as shown in FIG. 7C. The first and second canopy electrodes 402a, b are electrically coupled to an electrically conductive wire disposed within the cable 106 to couple the first and second canopy electrodes 402a, b to the energy source 119 previously described with reference to FIGS. 1-5. In one embodiment the first canopy electrode 402a may be configured as the anode (+) electrode coupled to the positive terminal of the energy source 119 and the second canopy electrode 402b may be configured as the cathode (−) electrode coupled to the negative terminal of the energy source 119. It will be appreciated that the polarity of the first and second canopy electrodes 402a, b may be reversed such that the first canopy electrode 402a is configured as the cathode (−) electrode and the second canopy electrode 402b is configured as the anode (+) electrode by reversing the output polarity of the energy source 119. In various other embodiments, the first and second canopy electrodes 404a, b of the electrical ablation device 400 may be coupled to the energy source 119 percutaneously through the abdominal wall 109 (FIG. 19) or wirelessly by replacing the cable 106 with the antenna 904 (FIG. 20). The antenna 904 is coupled to the first canopy electrode 404a by a first electrically conductive wire and the antenna 904 is coupled to the second canopy electrode 404b by a second electrically conductive wire.

The first and second canopy electrodes 402a, b have an umbrella-like structure such that each canopy electrode 402a, b can be independently opened and closed. In FIG. 11A, the first and second canopy electrodes 402a, b are shown in a closed position used for insertion through the tumor 110 and the liver 112. The first and second canopy electrodes 402a, b each comprise a plurality of ribs 406a, b, shown in cross-section, to support electrically conductive sheets 414a, b. The electrically conductive sheets 414a, b are attached to the respective plurality of ribs 406a, b. Each of the first and second canopy electrodes 402a, b comprises a plurality of stretchers 408a, b that are pivotally coupled to the ribs 406a, b on one end and pivotally coupled to movable runners 410a, b on the other end. The first and second canopy electrodes 402a, b may be opened and closed by slidably moving the runners 410a, b along shafts 412a, b. When the first and second canopy electrodes 402a, b are opened, the electrically conductive sheets 414a, b are stretched out in a substantially circular structure. FIG. 11D is a top-view of one embodiment of the first canopy electrode 402a of the electrical ablation device 400 shown in an open position. The second canopy electrode 402b assumes a similar structure when opened.

In the embodiment shown in FIG. 11A, the first and second canopy electrodes 402a, b are shown in a closed position. The first electrode canopy electrode 402a may be opened by slidably moving the runner 410a in direction C. The second canopy electrode 402b may be opened by slidably moving the runner 410b in direction D. A first shaft 416a is coupled to the first canopy electrode 402a and is slidably received within a second hollow shaft 416b. This allows the first and second canopy electrodes 402a, b to be pulled towards each other after they are opened to compress the liver 112. The first and second shafts 416a, b are formed of an electrically insulative material such as medical grade polyester, for example, to electrically isolate the first and second shafts 416a, b from the first and second canopy electrodes 402a, b.

Referring to FIGS. 11A-C, the illustrated embodiment of the electrical ablation device 400 is shown in use in treatment of the tumor 110 formed in the liver 112 using IRE energy. As shown in FIG. 11A, the first and second canopy electrodes 402a, b are folded in a closed position. The distal end 404 of the second canopy electrode 402a is inserted in direction C into one side of the liver 112, through the tumor 110, and out the other side of the liver 112. As shown in FIG. 11B, both the first and second canopy electrodes 402a, b are opened by slidably moving the respective runners 410a, b in the respective directions C and D as discussed above. When the first and second canopy electrodes 402a, b are opened, the stretchers 408a, b stretch out the electrically conductive sheets 414a, b. Then, the first canopy electrode 402a is pulled in direction D and the second canopy electrode 402b is pushed in direction C such that the first shaft 416a is slidably received within the second shaft 416b and the first and second canopy electrodes 402a, b are pulled adjacent to the outer surfaces of the liver 112, as shown in FIG. 11C. The first and second canopy electrodes 402a, b may be pulled towards each other to compress the portion of the liver 112 located therebetween. As shown in FIG. 11C the liver 112 may be slightly compressed such that $y_2 < y_1$, where $y_1$ is the pre-compressed thickness of the liver 112 and $y_2$ is the compressed thickness of the liver 112.

With reference to FIG. 11C, the tumor 110 may be electrically ablated by applying IRE energy to the electrode assembly 402 when the first and second electrodes 402a, b are deployed. As previously discussed, the energy source 119 (previously described with reference to FIGS. 1-5) supplies DC pulses at frequencies in the range of about 1 Hz to about 1000 Hz, amplitudes in the range of about ±100 to about ±3000 VDC, and pulse widths (e.g., pulse durations) in the range of about 1 µs to about 100 ms to the first and second canopy electrodes 402a, b. The polarity of the energy delivered to the first and second canopy electrodes 402a, b may be reversed during the electrical ablation therapy. For example, the polarity of the DC pulses initially delivered at amplitudes in the range of about +100 to about +3000 VDC may be reversed to amplitudes of about −100 to about −3000 VDC. Preferably, the tumor 110 may be electrically ablated with DC pulses at frequencies of about 10 Hz to about 100 Hz, amplitudes in the range of about +700 to about +1500 VDC, and pulse widths of about 10 µs to about 50 µs.

Figure 12:
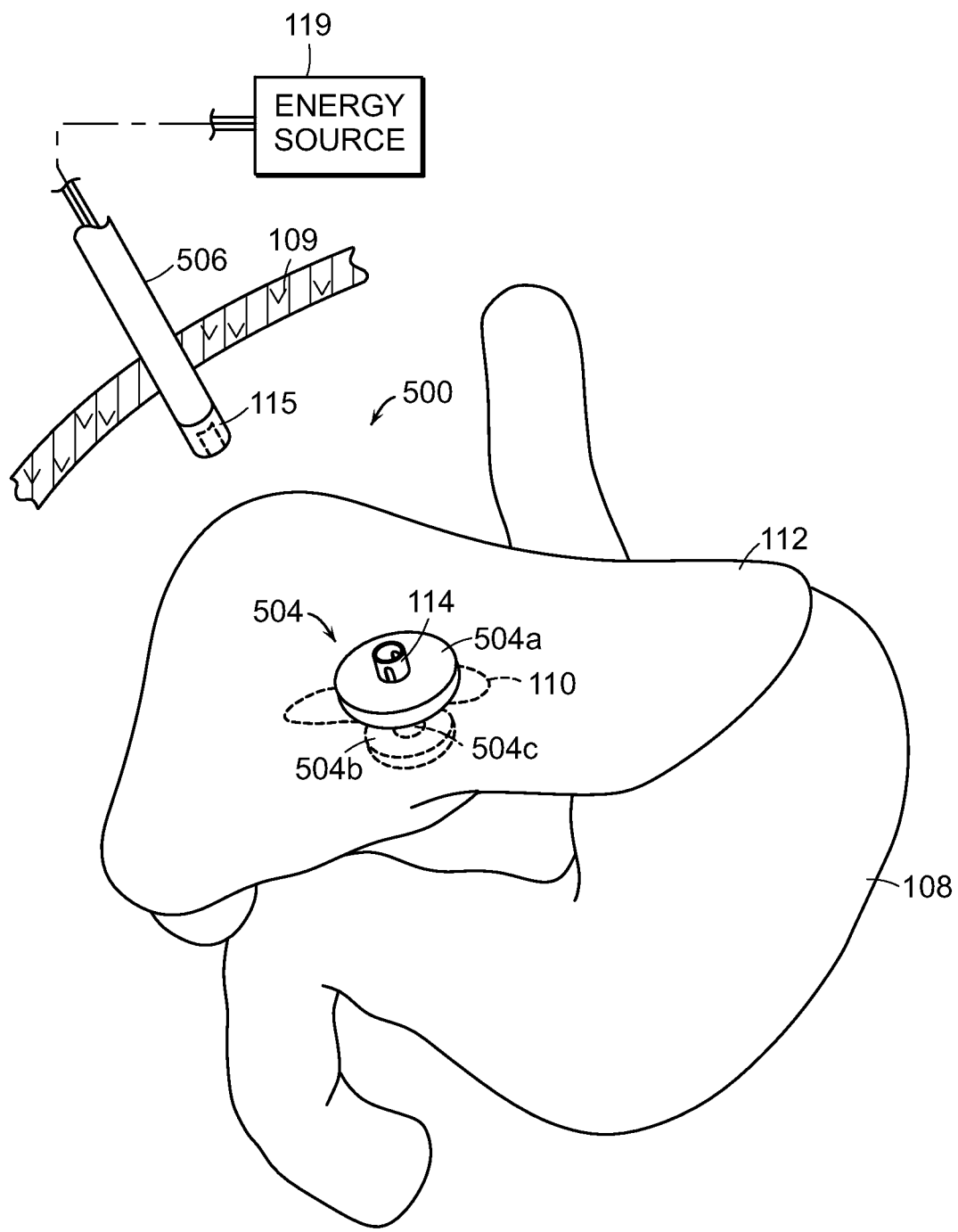
FIG. 12 illustrates one embodiment of an electrical ablation device attached to a solid organ prior to being connected to an energy source.

FIG. 12 illustrates one embodiment of an electrical ablation device 500 attached to a solid organ prior to being connected to the energy source 119 (previously described with reference to FIGS. 1-5). In one embodiment, the electrical ablation device 500 may be used in treatment of abnormal tissues or growths, such as cancers or tumors, formed in or on solid organs, BPH, and restricted gastric tissue using IRE energy. In other embodiments, electrical ablation treatment may be applied using other forms of electrical energy, such as those described herein. In the embodiment illustrated in FIG. 12, the electrical ablation device 500 comprises an electrode 504. The electrode 504 is configured for attachment to a solid organ, such as the liver 112. In the embodiment illustrated in FIG. 12, the electrode 504 is attached to the liver 112. The electrode 504 may be attached to the liver 112, or any solid organ, using a variety of fasteners. The electrode 504 comprises a first plate electrode 504a and a second plate electrode 504b and a center post 504c located therebetween. The first and second plate electrodes 504a, b each comprises at least one electrically conductive portion that is formed of or coated with an electrically conductive material such as medical grade stainless steel, for example, and are electrically coupled to respective first and second conductor portions of the cable 506 to deliver electrical ablation energy to the tumor 110 from the energy source 119. The center post 504c is inserted through the tumor 110 and the first and second plate electrodes 504a, b are positioned on either side of the tumor 110 on an outer surface of the liver 112. The center post 504c is formed of an electrically insulative material such as medical grade polyester, for example, to electrically isolate the center post 504c from the first and second plate electrodes 504a, b. In one embodiment the first plate electrode 504a may be configured as the anode (+) electrode coupled to the positive terminal of the energy source 119 and the second plate electrode 504b may be configured as the cathode (−) electrode coupled to the negative terminal of the energy source 119. It will be appreciated that the polarity of the first and second plate electrodes 504a, b may be reversed such that the first plate electrode 504a is configured as the cathode (−) electrode and the second plate electrode 504b is configured as the anode (+) electrode by reversing the output polarity of the energy source 119. In various other embodiments, the first and second plate electrodes 504a, b of the electrical ablation device 500 may be coupled to the energy source 119 percutaneously through the abdominal wall 109 (FIG. 19) or wirelessly by replacing the cable 106 with the antenna 904 (FIG. 20). The antenna 904 is coupled to the first plate electrode 504a by a first electrically conductive wire and the antenna 904 is coupled to the second plate electrode 504b by a second electrically conductive wire.

In the illustrated embodiment, the first plate electrode 504a is located above the tumor 110 and the second plate electrode 504b is located below the tumor 110. The first and second plate electrodes 504a, b are configured as electrodes. The first plate electrode 504a comprises a connector 114 to couple the electrode 504 to an energy source via an endoscopically, laparoscopically, transcutaneously, or percutaneously insertable cable 506 comprising the mating plug 115 to electrically couple to the connector 114. The first and second plate electrodes 504a, b are electrically coupled to respective first and second conductor portions of the cable 506, for example. In one embodiment, the first and second plate electrodes 504a, b may be introduced endoscopically, laparoscopically, or via open surgical procedures such as a laparotomy. As previously discussed, the cable 506 also may be introduced into the stomach 108 trans-orally through the access or working channel of the endoscope. In the illustrated embodiment, the cable 506 is inserted percutaneously through the abdominal wall 109.

With reference to FIG. 12, the tumor 110 may be electrically ablated by applying IRE energy to the electrode 504 when the first and second plate electrodes 504a, b are deployed. As previously discussed, the energy source 119 (previously described with reference to FIGS. 1-5) supplies DC pulses at frequencies in the range of about 1 Hz to about 1000 Hz, amplitudes in the range of about ±100 to about ±3000 VDC, and pulse widths (e.g., pulse durations) in the range of about 1 µs to about 100 ms to the first and second plate electrodes 504a, b of the electrode 504. The polarity of the energy delivered to the first and second plate electrodes 504a, b of the electrode 504 may be reversed during the electrical ablation therapy. For example, the polarity of the DC pulses initially delivered at amplitudes in the range of about +100 to about +3000 VDC may be reversed to amplitudes of about −100 to about −3000 VDC. Preferably, the tumor 110 may be electrically ablated with DC pulses at frequencies of about 10 Hz to about 100 Hz, amplitudes in the range of about +700 to about +1500 VDC, and pulse widths of about 10 µs to about 50 µs. The tumor 110 may be monitored over time (weeks) to observe shrinkage. The treatment may be repeated until the tumor 110 disappears.

FIG. 13 illustrates one embodiment of an electrical ablation device 600. In the illustrated embodiment, the electrical ablation device 600 comprises a balloon electrode 602 that can be inserted into the uterine cavity 638 (FIGS. 14A-B, 15A) for the treatment of menorrhagia using IRE energy. In other embodiments, electrical ablation treatment may be applied using other forms of electrical energy, such as those described herein. In other embodiments, the electrode may be implemented as a sponge or similar structure. In FIG. 13, there is shown a lateral cross-sectional view of the electrical ablation device 600. In one embodiment, the electrical ablation device 600 is primarily intended for non-surgical entry into the uterine cavity 638 of a female although one of ordinary skill in the art will recognize its usefulness in other related procedures. The electrical ablation device 600 has an elongate tubular body 610 extending from a distal end 612 to a proximal end 614. Located on the marginal distal end 612 of the body 610 is an inflatable intracervical/intrauterine balloon electrode 602. As shown in FIG. 13, the balloon electrode 602 is in a deflated state. A connector 628 for coupling the energy source 119 to the electrical ablation device 600 is located at a proximal end 620 of a conduit 604, which will be described in greater detail below.

Figure 15A:
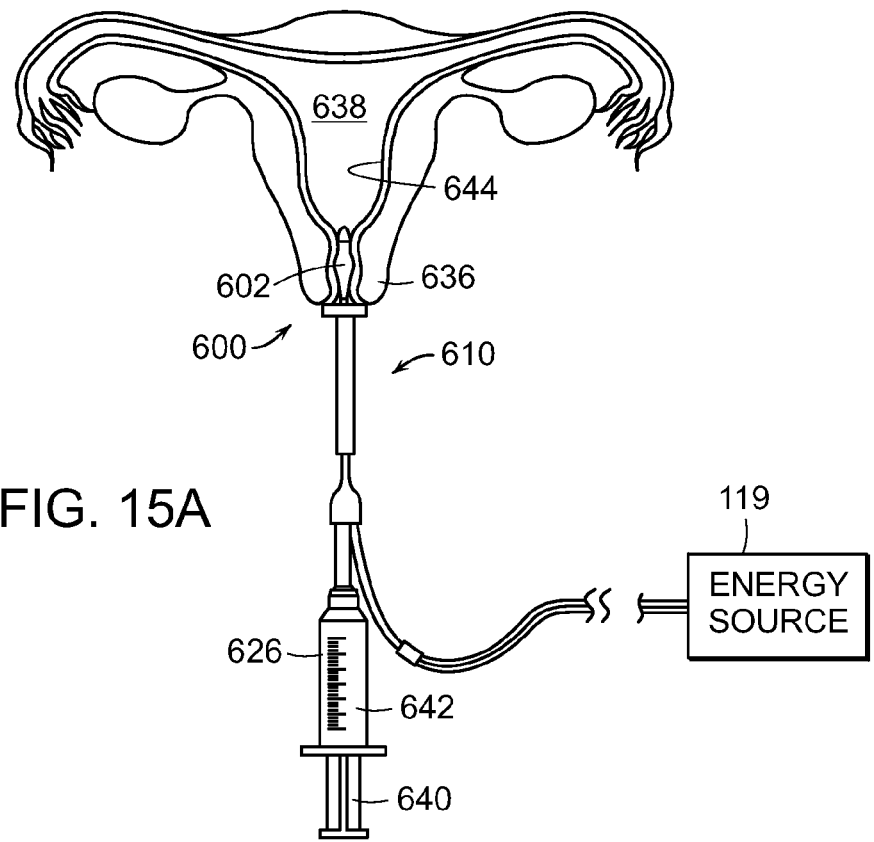
FIG. 15A illustrates one embodiment of an electrical ablation device shown in use entering the cervix with the balloon electrode in a deflated state.
Figure 15B:
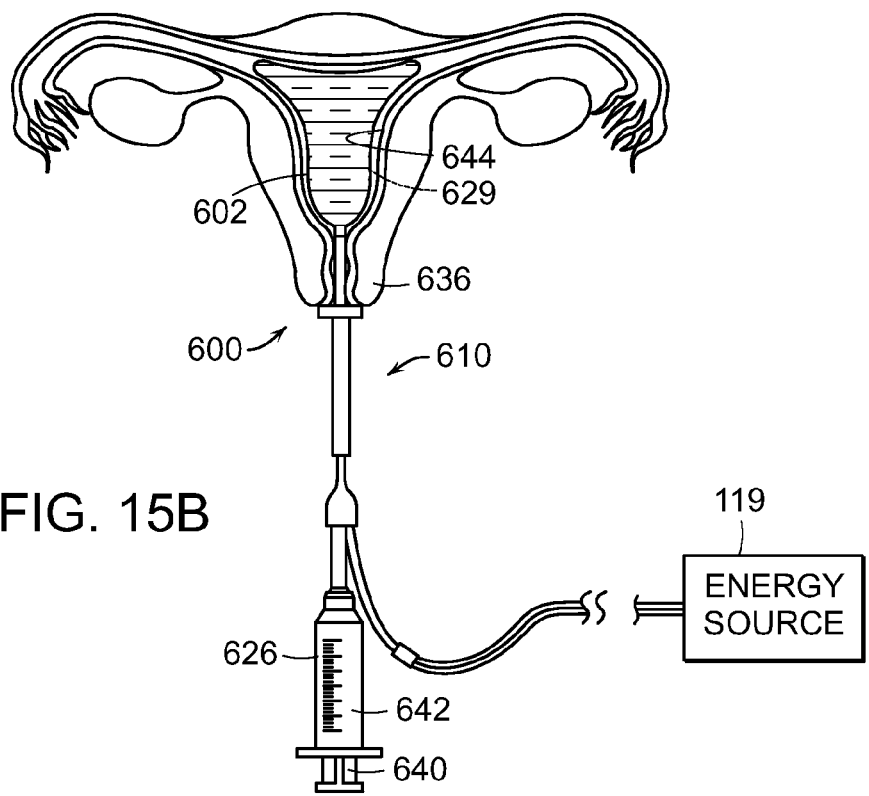
FIG. 15B illustrates one embodiment of the balloon electrode inserted through the cervix and into the uterine cavity in an inflated state.

In one embodiment, the electrical ablation device 600 also comprises an inflation fluid line 616 having a distal 622, which terminates within the body 610, and a proximal end 620. The inflation fluid line 616 enters the body 610 at a fluid line coupler 630. The proximal end 620 of the inflation fluid line 616 may be coupled to a conventional inline rotary valve (not shown) to control the flow of inflation fluid. A proximal end of the inline rotary valve is removably coupled to a conventional inflation syringe 626 (FIGS. 15A-B). A cylindrical collar member 632 is slidably mounted on the tubular body 610 between the balloon electrode 602 and the fluid line coupler 630. The collar member 632 comprises an outwardly extending circumferential flange 634 at its distal end.

As shown, the inner conduit 604 defines a working lumen 606 is disposed within the body 610 and extends the entire length of the body 610 from the distal end 612 to the proximal end 614. The working lumen 606 of the inner conduit 604 provides an electrical communication path for the introduction of one or more electrically conductive wires 608 for delivering electrical energy from the energy source 119 to the balloon electrode 602. The one ore more conductors 608 may be electrically coupled to the balloon electrode 602 to convey electrical energy from the energy source 119 thereto.

The inflation fluid line 616 defines an inflation lumen 618. The inflation lumen 618 starts at the proximal end 620 of the inflation fluid line 616 and extends therethrough to the distal end 622 thereof. The inflation lumen 618 fluidically communicates with the interior of the balloon electrode 602 via an aperture 624. The inflation lumen 618 of the inflation fluid line 616 provides a fluid communication path for inflating the balloon electrode 602 with a fluid 629 (FIG. 15A). The fluid 629 may be either saline or air or other suitable electrically conductive inflation fluid. An inline rotary valve (not shown) may operate to maintain the balloon electrode 602 in the inflated state after inflation by the inflation syringe 626 (FIGS. 15A, 15B). A port 639 may be defined at the distal end of the working lumen 406 to provide a fluid communication path between the working lumen 406 and the external portion of the balloon electrode 602 to deliver fluids into the hollow body lumen (e.g., the uterine cavity 638) outside of the balloon electrode 602.

FIGS. 14A and 14B show the progression of one embodiment of the electrical ablation device 600 penetrating through the cervix 636 and insertion into the uterine cavity 638. FIG. 14A illustrates the balloon electrode 602 in a deflated state inserted into the cervix 636. FIG. 14B illustrates the balloon electrode 602 inserted in the uterine cavity 638 in a partially inflated state. Once the balloon electrode 602 is inserted into the uterine cavity 638, the balloon electrode 602 may be fully inflated.

In FIG. 15A, the electrical ablation device 600 is shown in use entering the cervix 636 with the balloon electrode 602 in a deflated state. Once inserted through the cervix 636 and into the uterine cavity 638, as shown in FIG. 15B, the balloon electrode 602 is inflated by pushing the plunger 640 into the body 642 of the inflation syringe 626. The balloon electrode 602 is inflated with the fluid 629. Once the balloon electrode 602 is inflated, an inline rotary valve (not shown) may be rotated into a "closed position" to prevent communication between the inflation syringe 626 and the inflation lumen 618 (FIG. 13). When it is desirable to deflate the balloon electrode 602, the inline rotary valve may be rotated into an "open position" to reestablish communication between the inflation syringe 626 and the inflation lumen 618. To deflate the balloon electrode 602, the plunger 640 is pulled toward the proximal end of the body 642 of the inflation syringe 626. A conductive fluid may be injected around the balloon electrode 602 to expand the zone of treatment. The conductive fluid may be delivered through the port 639 (FIG. 13) into the uterine cavity 638 to expand the zone of treatment.

The various components of the electrical ablation device 600 are made from conventional materials such as nylon, polyethylene, or a composite. In one embodiment, the intracervical/intrauterine balloon electrode 602 is made from or comprises an electrically conductive material to transmit electrical energy from the energy source 119 to the internal walls 644 of the uterine cavity 638 for applying electrical ablation therapy thereto. In another embodiment, the intracervical/intrauterine balloon electrode 602 may be made from a medical grade polyurethane material comprising an electrically conductive coating on an outer surface thereof. In another embodiment, the balloon electrode 602 may be made from an electrically conductive material. In yet another embodiment, the balloon electrode 602 may be made from an electrically insulative material, such as the medical grade polyurethane, and inflated with a conductive fluid (e.g., saline) to form the electrically conductive portion of the balloon electrode 602. In one embodiment the balloon electrode 602 may be configured as the anode (+) electrode coupled to the positive terminal of the energy source 119 and in another embodiment the balloon electrode 602 may be configured as the cathode (−) electrode coupled to the negative terminal of the energy source 119. It will be appreciated that the polarity of the balloon electrode 602 may be reversed by reversing the output polarity of the energy source 119. In one embodiment, the balloon electrode 602 may be configured as either the anode (+) or the cathode (−) relative to a reference polarity. For example, the balloon electrode 602 may be configured as the cathode (+) coupled to the positive output of the energy source 119 relative to a ground plane cathode (−) located beneath the patient and coupled to the negative terminal of the energy source 119.

In the embodiment illustrated in FIGS. 14A-B and 15A-B, the electrical ablation device 600 is configured for use as an intrauterine device for treating menorrhagia through the use of electrical energy. In one embodiment, the balloon electrode 602 applies IRE energy supplied by the energy source 119. As previously described, IRE provides an effective method for destroying cells while avoiding some of the negative complications of heat-inducing therapies. Namely, IRE destroys cells without the use of heat and does not destroy cellular support structure or regional vasculature. In the illustrated embodiment, the balloon electrode 602 can be inserted into the uterine cavity 638 and once placed therein the balloon electrode 602 can be expanded or inflated with the fluid 629 to make substantially complete contact with the uterine wall 644.

After the balloon electrode 602 is inflated, electrical ablation energy is supplied by the energy source 119 to electrically ablate the internal walls 644 of the uterine cavity 638 to treat menorrhagia by applying IRE energy to the balloon electrode 602. As previously discussed, the energy source 119 (previously described with reference to FIGS. 1-5) supplies DC pulses at frequencies in the range of about 1 Hz to about 1000 Hz, amplitudes in the range of about ±100 to about ±3000 VDC, and pulse widths (e.g., pulse durations) in the range of about 1 μs to about 100 ms to the balloon electrode 602. The polarity of the energy delivered to the balloon electrode 602 may be reversed during the electrical ablation therapy. For example, the polarity of the DC pulses initially delivered at amplitudes in the range of about +100 to about +3000 VDC may be reversed to amplitudes of about −100 to about −3000 VDC. Preferably, the internal walls 644 of the uterine cavity 638 may be electrically ablated with DC pulses at frequencies of about 10 Hz to about 100 Hz, amplitudes in the range of about +700 to about +1500 VDC, and pulse widths of about 10 μs to about 50 μs. Multiple placements of the balloon electrode 602 can be performed to treat large areas of the uterus. A conductive fluid may be injected around the balloon electrode 602 to expand the zone of treatment for a given irreversible electroporation treatment. The menorrhagia may be monitored over time (weeks) to observe the effectiveness of the electrical ablation therapy. The treatment may be repeated until the menorrhagia disappears.

Figure 16:
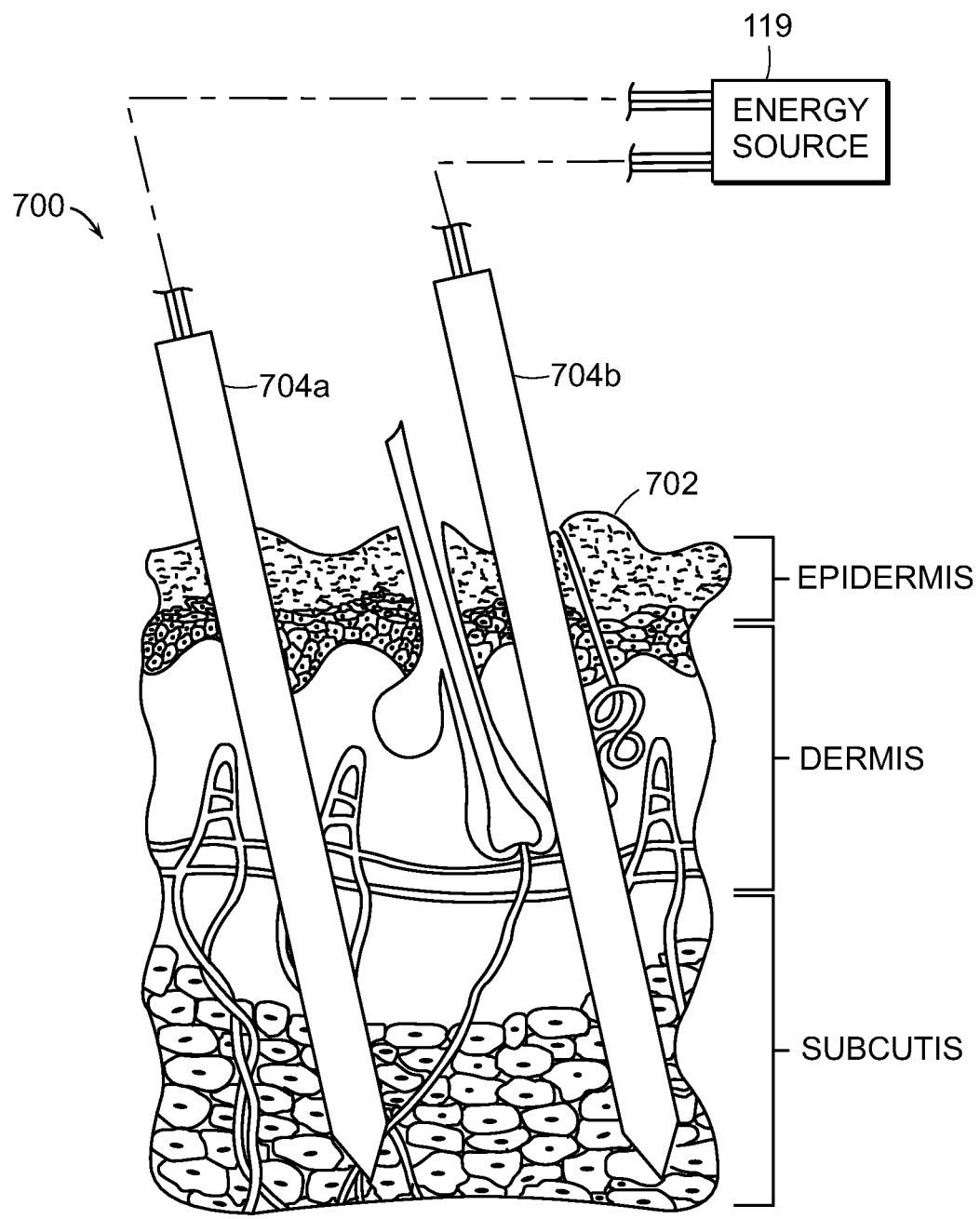
FIG. 16 illustrates one embodiment of an electrical ablation device for removing excess skin.

FIG. 16 illustrates one embodiment of an electrical ablation device 700 for removing excess skin 702 using IRE energy. In other embodiments, electrical ablation treatment may be applied using other forms of electrical energy, such as those described herein. The electrical ablation device 700 may be used in minimally invasive therapy for removal of the excess skin 702 following excess weight loss due to bariatric surgery. This therapy involves the administration of IRE energy pulses to excess skin 702 at various sites on a patient's body. As previously described with reference to FIGS. 1-5, the IRE energy pulses may be supplied by the energy source 119. In the embodiment illustrated in FIG. 16, the electrical ablation device 700 comprises needle electrodes 704a, 704b that may be inserted through the skin 702. The needle electrodes 704a, b each comprises at least one electrically conductive portion that is formed of or coated with an electrically conductive material such as medical grade stainless steel, for example. In one embodiment the first needle electrode 704a may be configured as the anode (+) electrode coupled to the positive terminal of the energy source 119 and the second needle electrode 704b may be configured as the cathode (−) electrode coupled to the negative terminal of the energy source 119. It will be appreciated that the polarity of the first and second needle electrodes 704a, b may be reversed such that the first needle electrode 704a is configured as the cathode (−) electrode and the second needle electrode 704b is configured as the anode (+) electrode by reversing the output polarity of the energy source 119. It will be appreciated that a plurality of needle electrodes may be employed. Once the needle electrodes 704a, b are inserted at the appropriate level below the outer epidermis layer of the skin 702, IRE energy pulses may be administered to the needle electrodes 704a, b by the energy source 119 to destroy the cells of the epidermis, dermis, and subcutis layers of the skin 702. The needle electrodes 704a, b may be moved to various locations on the excess skin 702 flap, and the treatment repeated.

The therapeutic treatments administered using the embodiments of the electrical ablation device 700 illustrated in FIG. 16 result in a reduction in the surface area of the skin 702. The therapy may be administered over several weeks or months, with each therapy resulting in the gradual removal of the excess skin 702. The electrical ablation energy is supplied by the energy source 119. As previously discussed, the energy source 119 (previously described with reference to FIGS. 1-5) supplies DC pulses at frequencies in the range of about 1 Hz to about 1000 Hz, amplitudes in the range of about ±100 to about ±3000 VDC, and pulse widths (e.g., pulse durations) in the range of about 1 μs to about 100 ms to the needle electrodes 704a, b. The polarity of the energy delivered to the needle electrodes 704a, b may be reversed during the electrical ablation therapy. For example, the polarity of the DC pulses initially delivered at amplitudes in the range of about +100 to about +3000 VDC may be reversed to amplitudes of about −100 to about −3000 VDC. Preferably, the excess skin 702 may be electrically ablated with DC pulses at frequencies of about 10 Hz to about 100 Hz, amplitudes in the range of about +700 to about +1500 VDC, and pulse widths of about 10 μs to about 50 μs. Multiple placements of the needle electrodes 704a, b can be performed to treat large areas of the excess skin 702.

Figure 17:
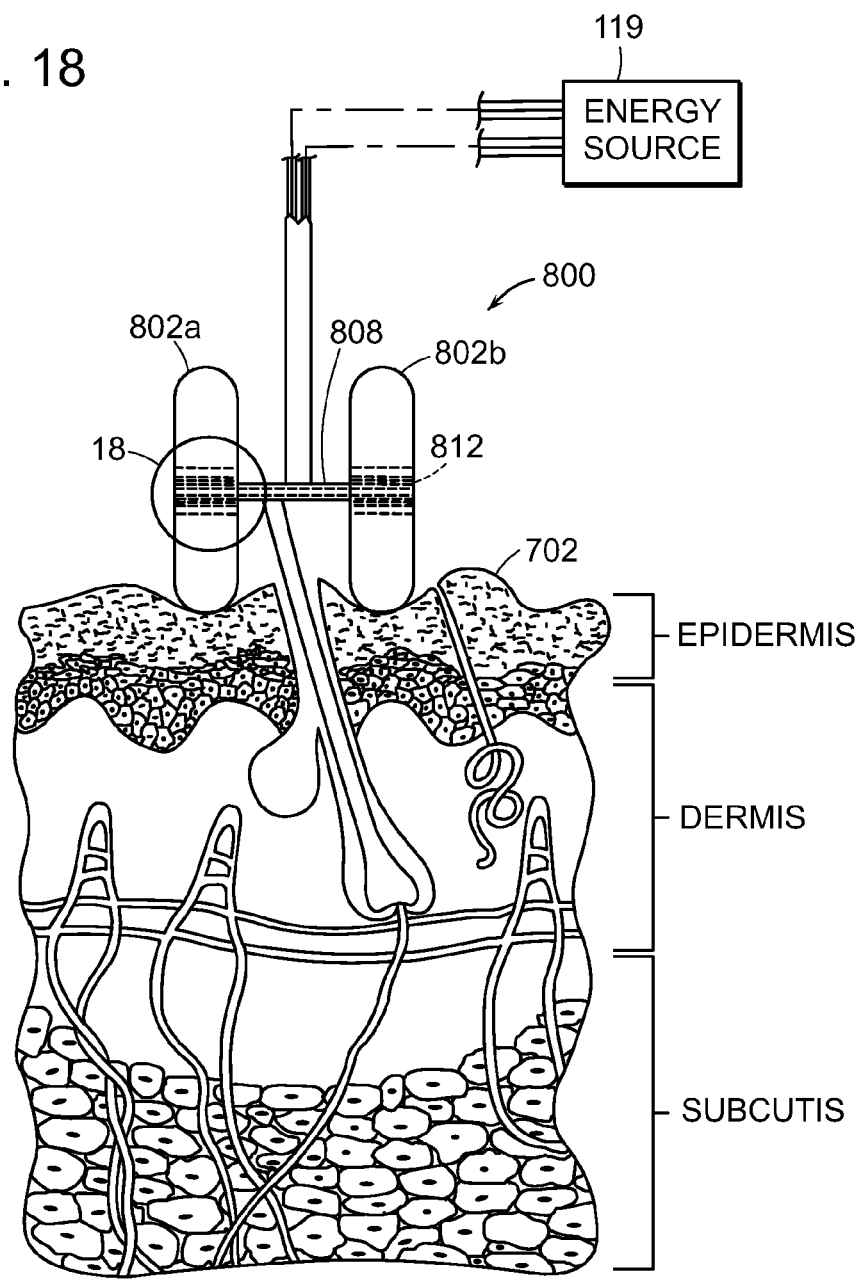
FIG. 17 illustrates one embodiment of an electrical ablation device for removing excess skin.

FIG. 17 illustrates one embodiment of an electrical ablation device 800 for removing excess skin 702. In one embodiment, the excess skin 702 may be removed using IRE energy. In other embodiments, electrical ablation treatment may be applied using other forms of electrical energy, such as those described herein. The electrical ablation device 800 may be used in minimally invasive therapy for removal of the excess skin 702 that normally follows excess weight loss due to bariatric surgery. In the embodiment illustrated in FIG. 17, first and second electrodes 802a, 802b are configured as rollers (first and second roller electrodes 802a, b). The first and second electrodes 802a, b have a substantially circular or disk-like body defining a hub 812 and are arranged to rotate about an axis. The IRE energy pulses from the energy source 119 (previously described with reference to FIGS. 1-5) are administered as the first and second roller electrodes 802*a, b* move over the patient's skin 702. The IRE energy destroys the cells in the epidermis and the dermis layers of the skin 702. In one embodiment the first roller electrode 802*a* may be configured as the anode (+) electrode coupled to the positive terminal of the energy source 119 and the second roller electrode 802*b* may be configured as the cathode (−) electrode coupled to the negative terminal of the energy source 119. It will be appreciated that the polarity of the first and second roller electrodes 802*a, b* may be reversed such that the first roller electrode 802*a* is configured as the cathode (−) electrode and the second roller electrode 802*b* is configured as the anode (+) electrode by reversing the output polarity of the energy source 119. In one embodiment, both the first and second roller electrodes 802*a, b* may be coupled to the same polarity and may be configured as the anode (+) or the cathode (−) relative to a reference polarity. For example, the first and second roller electrodes 802*a, b* may be configured as the cathode (+) coupled to the positive output of the energy source 119 relative to a ground plane cathode (−) located beneath the patient and coupled to the negative terminal of the energy source 119.

Figure 18:
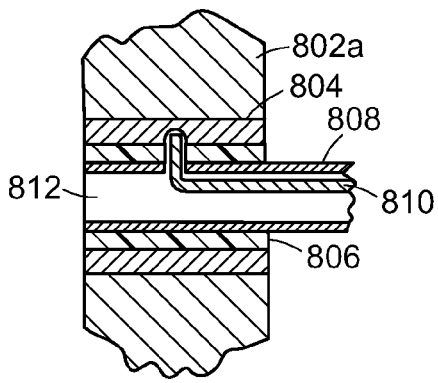
FIG. 18 is a detail cross-sectional view of one embodiment of one embodiment of the electrode shown in FIG. 17.

FIG. 18 is a detail cross-sectional view of one embodiment of the electrode 802*a*. Those skilled in the art will appreciate that the roller electrode 802*b* may be constructed in a similar fashion. As shown in FIG. 18, the roller electrode 802*a* comprises a body having at least one electrically conductive portion at an outer surface thereof that is formed of or coated with an electrically conductive material (e.g., copper, aluminum, brass, steel, medical grade stainless steel). The roller electrode 802*a* rotates about a cylindrical bearing 804 positioned within the hub 812. The cylindrical bearing 804 is formed of an electrically conductive material and is in electrical communication with the electrically conductive portion of the roller electrode 802*a* body. An electrically insulative sleeve 806 formed of medical grade polyester, for example, is positioned between the cylindrical bearing 804 and a shaft 808. The shaft 808 is received within the hub 812 and defines as an axis of rotation for the roller electrode 802*a*. An electrically conductive wire 810 is electrically coupled to the bearing 804 and thus to the roller electrode 802*a*. Electrical energy from the energy source 119 is conducted via the conductor 810 to the roller electrode 802*a*. The embodiments of the roller electrodes 802*a, b* are not limited in this context.

The therapeutic treatments administered using the embodiments of the electrical ablation device 800 illustrated in FIGS. 17 and 18 result in a reduction in the surface area of the skin 702. The therapy may be administered over several weeks or months, with each therapy resulting in the gradual removal of the excess skin 702. The electrical ablation energy is supplied by the energy source 119. As previously discussed, the energy source 119 (previously described with reference to FIGS. 1-5) supplies DC pulses at frequencies in the range of about 1 Hz to about 1000 Hz, amplitudes in the range of about ±100 to about ±3000 VDC, and pulse widths (e.g., pulse durations) in the range of about 1 μs to about 100 ms to the roller electrodes 802*a, b*. The polarity of the energy delivered to the roller electrodes 802*a, b* may be reversed during the electrical ablation therapy. For example, the polarity of the DC pulses initially delivered at amplitudes in the range of about +100 to about +3000 VDC may be reversed to amplitudes of about −100 to about −3000 VDC. Preferably, the excess skin 702 may be electrically ablated with DC pulses at frequencies of about 10 Hz to about 100 Hz, amplitudes in the range of about +700 to about +1500 VDC, and pulse widths of about 10 μs to about 50 μs. Multiple placements of the roller electrodes 802*a, b* can be performed to treat large areas of the excess skin 702.

FIG. 20 illustrates one embodiment of a wireless electrical ablation device 900 shown in use. The electrical ablation device 900 comprises one or more electrodes 902 connected to an antenna 904. In various embodiments, the one or more electrodes 902 may be configured as any one of the previously discussed electrodes 100, 200, 300, 400, 500, 600. In one embodiment, the energy source 119 may comprise a wireless transmitter 906 configured to deliver energy 910 to the one or more electrodes 902 via an antenna 908. The energy source 119 transmits the energy 910 through the transmitting antenna 908, which is received by the antenna 904, thus eliminating the need to perforate the hollow body lumen or the patient's skin. The embodiments are not limited in this context.

The various embodiments of the electrical ablation devices and techniques described herein may be employed in electrical ablation therapy of tissue. Embodiments of the electrical ablation devices and techniques described herein may be employed in treatment or removal of diseased tissue, restricted gastric tissue, adipose tissue, abnormal tissue masses, tumors, lesions, adhesions, BPH, and menorrhagia, among others, located inside the patient's body using electrical ablation energy. Other embodiments of the electrical ablation devices described herein may be employed in treatment or removal of excess skin following bariatric surgery using electrical ablation energy.

The embodiments of the electrical ablation devices described herein may be introduced inside a patient using minimally invasive or open surgical techniques. In some instances it may be advantageous to introduce the electrical ablation devices inside the patient using a combination of minimally invasive and open surgical techniques. Minimally invasive techniques provide more accurate and effective access to the treatment region for diagnostic and treatment procedures. To reach internal treatment regions within the patient, the electrical ablation devices described herein may be inserted through natural openings of the body such as the mouth, anus, and/or vagina, for example. Minimally invasive procedures performed by the introduction of various medical devices into the patient through a natural opening of the patient are known in the art as Natural Orifice Translumenal Endoscopic Surgery (NOTES™) procedures. Surgical devices, such as an electrical ablation devices, may be introduced to the treatment region through the working channels of the endoscope to perform key surgical activities (KSA), including, for example, electrical ablation of tissues using IRE energy. Some portions of the electrical therapy ablation devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina). A rigid endoscope may be introduced via trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Once an electrical ablation device is inserted in the human body internal organs may be reached using trans-organ or translumenal surgical procedures. The electrical ablation device may be advanced to the treatment site using endoscopic translumenal access techniques to perforate a lumen, and then, advance the electrical ablation device and the endoscope into the peritoneal cavity. Translumenal access procedures for perforating a lumen wall, inserting, and advancing an endoscope therethrough, and pneumoperitoneum devices for insufflating the peritoneal cavity and closing or suturing the perforated lumen wall are well known. During a translumenal access procedure, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A guidewire is then feed through the endoscope and is passed through the puncture in the stomach wall and into the peritoneal cavity. The needle knife is removed, leaving the guidewire as a placeholder. A balloon catheter is then passed over the guidewire and through the working channel of the endoscope to position the balloon within the opening in the stomach wall. The balloon can then be inflated to increase the size of the opening, thereby enabling the endoscope to push against the rear of the balloon and to be feed through the opening and into the peritoneal cavity. Once the endoscope is positioned within the peritoneal cavity, numerous procedures can be performed through the working channel of the endoscope.

The endoscope may be connected to a video camera (single chip or three chip) and may be attached to a fiber-optic cable system connected to a "cold" light source (halogen or xenon), to illuminate the operative field. The video camera provides a direct line-of-sight view of the treatment region. The abdomen is usually insufflated with carbon dioxide ($CO_2$) gas to create a working and viewing space. The abdomen is essentially blown up like a balloon (insufflated), elevating the abdominal wall above the internal organs like a dome. $CO_2$ gas is used because it is common to the human body and can be removed by the respiratory system if it is absorbed through tissue.

Once the electrical ablation devices are located at the target site, the diseased tissue may be electrically ablated or destroyed using the various embodiments of electrodes discussed herein. The placement and location of the electrodes can be important for effective and efficient electrical ablation therapy. For example, the electrodes may be positioned proximal to a treatment region (e.g., target site or worksite) either endoscopically or transcutaneously (percutaneously). In some implementations, it may be necessary to introduce the electrodes inside the patient using a combination of endoscopic, transcutaneous, and/or open techniques. The electrodes may be introduced to the tissue treatment region through a working channel of the endoscope, an overtube, or a trocar and, in some implementations, may be introduced through percutaneously or through small—keyhole—incisions.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, said to be incorporated by reference herein, but which conflicts with existing definitions, statements, or other disclosure material set forth herein will only be incorporated to the extent that no conflict arises between that incorporated material and the existing disclosure material.

The invention claimed is:

1. An electrical ablation apparatus, comprising:
    a connector configured to receive electrical energy from an energy source, the connector selectively connectable to a wire extending from the energy source;
    a fastener coupled to the connector, the fastener configured for attachment through a tissue wall; and
    a first electrode comprising at least one electrically conductive portion coupled to the connector by a first electrically conductive wire.

2. The electrical ablation apparatus of claim 1, wherein the connector comprises:
    a body comprising at least one recess for receiving at least one corresponding tab;
    at least one terminal;
    a first flange comprising at least one opening for receiving a suture or tag for attaching the connector to the tissue wall;
    a second flange comprising at least one opening for receiving a suture or tag for attaching the connector to the tissue wall; and
    a hollow shaft connecting the first and second flanges, the hollow shaft defining a longitudinal opening for receiving the at least one electrically conductive wire therethrough, wherein a first end of the at least one electrically conductive wire is connected to the at least one terminal.

3. The electrical ablation apparatus of claim 1, wherein the first electrode comprises a tapered body.

4. The electrical ablation apparatus of claim 3, wherein the tapered body comprises ridges formed on an outer surface to penetrate and attach the at least one electrode proximal to tissue to be ablated.

5. The electrical ablation apparatus of claim 1, wherein the first electrode comprises a helical body to penetrate and attach the first electrode proximal to tissue to be ablated.

6. The electrical ablation apparatus of claim 1, comprising:
a second electrode comprising at least one electrically conductive portion coupled to the connector by a second electrically conductive wire.

\* \* \* \* \*